(12) United States Patent
Joo et al.

(10) Patent No.: US 8,865,919 B2
(45) Date of Patent: Oct. 21, 2014

(54) SULFONIUM COMPOUND, PHOTO-ACID GENERATOR, AND METHOD FOR MANUFACTURING THE SAME

(75) Inventors: Hyun Sang Joo, Seo-gu (KR); Dong Chul Seo, Chungcheongnam-do (KR); Dae Kyung Yoon, Daejeon (KR); Dae Hyeon Shin, Seoul (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 153 days.

(21) Appl. No.: 13/341,102

(22) Filed: Dec. 30, 2011

(65) Prior Publication Data

US 2012/0172606 A1 Jul. 5, 2012

(30) Foreign Application Priority Data

Jan. 3, 2011 (KR) .................. 10 2011 0000264

(51) Int. Cl.
| | |
|---|---|
| C07D 333/48 | (2006.01) |
| G03F 7/004 | (2006.01) |
| C07C 309/06 | (2006.01) |
| C07C 309/12 | (2006.01) |
| C07D 333/46 | (2006.01) |
| C07D 307/64 | (2006.01) |
| C07C 381/12 | (2006.01) |
| G03F 7/039 | (2006.01) |

(52) U.S. Cl.
CPC ............ *C07D 307/64* (2013.01); *G03F 7/0395* (2013.01); *G03F 7/0045* (2013.01); *C07C 309/06* (2013.01); *C07C 2103/74* (2013.01); *C07C 309/12* (2013.01); *G03F 7/0046* (2013.01); *G03F 7/397* (2013.01); *C07D 333/46* (2013.01); *C07C 381/12* (2013.01)
USPC .......................................................... 549/60

(58) Field of Classification Search
CPC ..................................................... C07D 307/64
USPC ..................................................... 549/59, 60
See application file for complete search history.

(56) References Cited

U.S. PATENT DOCUMENTS

| 4,883,740 A | 11/1989 | Schwalm et al. |
| 2004/0087690 A1 | 5/2004 | Lamanna et al. |
| 2010/0136479 A1 | 6/2010 | Yamaguchi et al. |

FOREIGN PATENT DOCUMENTS

| EP | 1158363 | 11/2001 |
| EP | 1199603 | 4/2002 |
| EP | 1308781 | 5/2003 |
| EP | 1662319 | 5/2006 |
| EP | 1688468 | 8/2006 |
| EP | 1710230 | 10/2006 |
| EP | 1975212 | 10/2008 |
| EP | 1703326 | 3/2010 |
| JP | 07092675 | 7/1995 |
| JP | 10039500 | 2/1998 |
| JP | 2003015296 | 1/2003 |
| JP | 2006178437 | 7/2006 |
| JP | 2006232968 | 9/2006 |
| JP | 2008081470 | 4/2008 |
| JP | 2009227934 | 10/2009 |
| WO | WO 2007007175 | 1/2007 |

OTHER PUBLICATIONS

King, Med. Chem., Principle and Practice (1994), pp. 206-208.*

* cited by examiner

*Primary Examiner* — Taofiq A Solola
(74) *Attorney, Agent, or Firm* — Davidson, Davidson & Kappel, LLC

(57) ABSTRACT

A sulfonium compound represented by formula (1), a photo-acid generator, and a method for producing a sulfonium compound are provided:

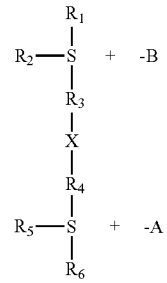

[Chemical Formula 1]

wherein X represents an electron-donating group; $R_1$ and $R_2$ each represent an alkyl group, a cycloalkyl group, or the like; $R_3$ and $R_4$ each represent an arylene group or a heteroarylene group; $R_5$ and $R_6$ each represent an alkyl group, a cycloalkyl group, or the like; and $A^-$ and $B^-$ are anions that are different from each other. The sulfonium compound, when used as a photo-acid generator, can produce a uniform and excellent resist pattern.

2 Claims, No Drawings

SULFONIUM COMPOUND, PHOTO-ACID GENERATOR, AND METHOD FOR MANUFACTURING THE SAME

BACKGROUND OF THE INVENTION

1. Field of the Invention

The present invention relates to a sulfonium compound having two acid sites that produce two different photo-acid generators in one molecule, a photo-acid generator containing the sulfonium compound, and a method for producing the photo-acid generator. More particularly, the present invention relates to a sulfonium compound which can address the problem of using a mixture of two different photo-acid generators, has excellent compatibility with the resist, and can produce an excellent resist pattern when applied as a photo-acid generator, and to a photo-acid generator containing the sulfonium compound, and a method for producing the sulfonium compound.

2. Description of Related Art

Semiconductor microprocessing technologies utilize lithographic processes, and in such lithographic processes, chemically amplified resist compositions are extensively used. Such a chemically amplified resist composition contains a photo-acid generator, which is a compound capable of generating an acid when irradiated with light.

When such a photo-acid generator absorbs light that is irradiated in a semiconductor patterning process, the photo-acid generator generates an acid.

In the case of an onium salt, which is one of photo-acid generators, the onium salt is degraded into a cation form or a radical form as a result of light irradiation, and exits in a different molecular form, and an acid is generated at the anion side, so that diffusion of acid occurs on the resist film at the time of wafer baking after light irradiation.

The photo-acid generator exerts direct influence on the resist pattern characteristics such as the resolution and line edge roughness (LER) of resists, due to various characteristic factors such as the ability to absorb light, the acid generation efficiency, the diffusion capability of the generated acid, and the strength of the anionic acid.

A conventional photo-acid generator has a molecular structure which is capable of generating only one type of acid. Thus, in order to obtain a high degree of resolution, when acid generators having all of the characteristics such as high diffusibility, low diffusibility, high permeability and low permeability are needed, the process of mixing acid generators and using a mixture thereof has been complicated and troublesome. Furthermore, in the case of using a mixture of acid generators, the acid generators may not be uniformly mixed in the resist, thereby rather causing a problem that a resist pattern having uniform characteristics cannot be obtained.

As an example of existing photo-acid generators, Korean Patent Application No. 10-2006-00133676 discloses a compound represented by the following formula:

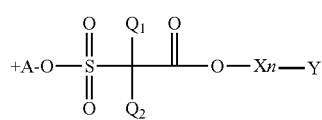

[Chemicla Formula]

wherein X represents an alkylene group or a substituted alkylene group; Y represents a hydrocarbon group having 5 to 30 carbon atoms and containing one or more aromatic rings; $Q_1$ and $Q_2$ each independently represent a fluorine atom or a perfluoroalkyl group having 1 to 6 carbon atoms; $A^+$ represents an organic counterion; and n represents 0 or 1.

In another example, Korean Patent Application No. 10-2007-0062926 filed by Shin-Etsu Chemical Co., Ltd. discloses a compound represented by the following formula:

[Chemical Formula]

wherein $R_1$ represents an alkyl group having 1 to 20 carbon atoms, an aryl group having 6 to 15 carbon atoms, or a heteroaryl group having 4 to 15 carbon atoms; and $M^+$ represents a lithium ion, a sodium ion, a potassium ion, an ammonium ion, or a tetramethylammonium ion.

It is described in the patent application filed by Shin-Etsu Chemical Co., Ltd. that the sulfonic acid represented by the above formula can exhibit strong acidity and can have a variety of substituents introduced thereinto, and that the degree of freedom in the design of molecule is high.

However, the conventional constitutions of photo-acid generators have problems that, in order to obtain high resolution, a photo-acid generator having a high diffusion rate and a photo-acid generator having a low diffusion rate, and a photo-acid generator having high permeability and a photo-acid generator having low permeability need to be used in mixture. Thus, when two or more kinds of photo-acid generators are used as a mixture in order to obtain a photo-acid generator having contradictory characteristics as described above, there is a problem that it is difficult to obtain uniform compatibility in the resist.

SUMMARY OF THE INVENTION

An object of the present invention is to provide a sulfonium compound which can give a pattern with high resolution and has uniform and excellent compatibility with other components in the resist, a photo-acid generator, and a method for producing the sulfonium compound.

According to an aspect of the present invention, there is provided a sulfonium compound represented by the following formula (1):

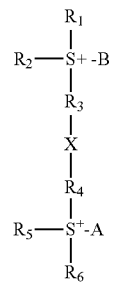

[Chemical Formula 1]

wherein in the formula (1),

X represents an electron-donating group;

$R_1$ and $R_2$ each independently represent any one selected from the group consisting of an alkyl group, a cycloalkyl group, an aryl group, a heteroaryl group, a heterocycloalkyl group and a heteroaryl group, or $R_1$ and $R_2$ may be joined, together with the sulfur atom to which $R_1$ is bonded, to form a heterocycloalkyl group having 2 to 7 carbon atoms;

$R_3$ and $R_4$ each independently represent any one selected from the group consisting of an arylene group and a heteroarylene group;

$R_5$ and $R_6$ each independently represent any one selected from the group consisting of an alkyl group, a cycloalkyl group, an aryl group, a heteroalkyl group, a heterocycloalkyl group and a heteroaryl group, or $R_5$ and $R_6$ may be joined, together with the sulfur atom to which $R_5$ is bonded, to form a heterocycloalkyl group having 2 to 7 carbon atoms; and $A^-$ and $B^-$ represent anions that are different from each other.

The anions $A^-$ and $B^-$ may each independently represent any one selected from the group consisting of a sulfonate anion, an imide anion, a methide anion, an alkyl halide anion, a carboxylate anion, an iodonium anion and a sulfonylimide anion.

The anions $A^-$ and $B^-$ may each independently represent any one selected from the group selected from the group consisting of anionic moieties represented by the following formulas (1-1), (1-2) and (1-3):

[Chemical Formula 1-1]

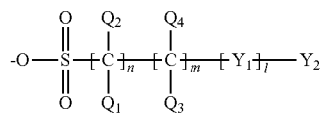

wherein in the formula (1-1), $Q_1$, $Q_2$, $Q_3$ and $Q_4$ each independently represent any one selected from the group consisting of a hydrogen atom, a halogen atom, and an alkyl group; $Y_1$ represents any one selected from the group consisting of an alkanediyl group, an alkenediyl group, NR', S, O, CO and combinations thereof; R' represents any one selected from the group consisting of a hydrogen atom and an alkyl group; $Y_2$ represents any one selected from the group consisting of a hydrogen atom, an alkyl group, a heterocycloalkyl group, an aryl group, a heteroaryl group, an alkyl group, a heteroalkyl group, an allyl group, a perfluoroalkyl group, a haloalkyl group and an alkylsulfonyl group; n represents an integer from 0 to 10; m represents an integer from 0 to 10; and l represents an integer from 0 to 5;

[Chemical Formula 1-2]

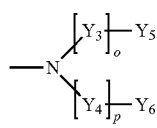

wherein in the formula (1-2), $Y_3$ and $Y_4$ each independently represent any one selected from the group consisting of an alkanediyl group, an alkenediyl group, NR', S, O, CO, $O_2S$ and combinations thereof; R' represents any one selected from the group consisting of a hydrogen atom and an alkyl group; $Y_5$ and $Y_6$ each independently represent any one selected from the group consisting of a hydrogen atom, an alkyl group, a heterocycloalkyl group, an aryl group, a heteroaryl group, an alkyl group, a heteroalkyl group, an allyl group, a perfluoroalkyl group, a haloalkyl group and an alkylsulfonyl group; o represents an integer from 0 to 5; and p represents an integer from 0 to 5; and

[Chemical Formula 1-3]

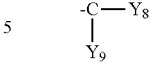

wherein in the formula (1-3), $Y_7$, $Y_8$ and $Y_9$ each independently represent any one selected from the group consisting of a hydrogen atom, an alkyl group, a heterocycloalkyl group, an aryl group, a heteroaryl group, an alkyl group, a heteroalkyl group, an allyl group, a perfluoroalkyl group, a haloalkyl group and an alkylsulfonyl group.

The anions A– and B– may each independently represent any one selected from the group consisting of $OSO_2CF_3^-$, $OSO_2C_4F_9^-$, $OSO_2C_8F_{17}^-$, $N(CF_3)_2^-$, $N(C_2F_5)_2^-$, $N(C_4F_9)_2^-$, $C(CF_3)_3^-$, $C(C_2F_5)_3^-$, $C(C_4F_9)_3^-$ and an anionic moiety represented by the following formula (1-4):

[Chemical Formula 1-4]

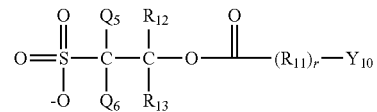

wherein in the formula (1-4), $Y_{10}$ represents any one selected from the group consisting of a cycloalkyl group, a heterocycloalkyl group, an aryl group, a heteroaryl group, an alkyl group, a heteroalkyl group, an allyl group, a perfluoroalkyl group, a haloalkyl group and an alkylsulfonyl group; $R_{11}$ represents any one selected from the group consisting of an alkanediyl group, an alkenediyl group, NR', S, O, CO and combinations thereof; R' represents any one selected from the group consisting of a hydrogen atom and an alkyl group; $R_{12}$ and $R_{13}$ each independently represent any one selected from the group consisting of a hydrogen atom and an alkyl group having 1 to 8 carbon atoms; r represents an integer from 0 to 5; $Q_5$ and $Q_6$ each independently represent a halogen atom.

$A^-$ may be any one selected from the group consisting of $OSO_2CF_3^-$, $OSO_2CF_2CF_2CF_2CF_3^-$ and an anionic moiety represented by the following formula (1-5), and the anion $B^-$ may be any one selected from the group consisting of $OSO_2CF_3^-$, $OSO_2CF_2CF_2CF_2CF_3^-$ and an anionic moiety represented by the following formula (1-5):

[Chemical Formula 1-5]

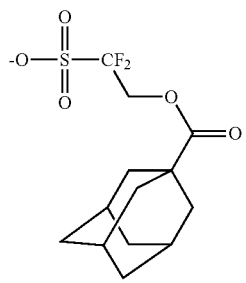

$R_3$ and $R_4$ may each independently represent any one selected from the group consisting of groups represented by the following formulas (2-1) and (2-2):

[Chemical Formula 2-1]

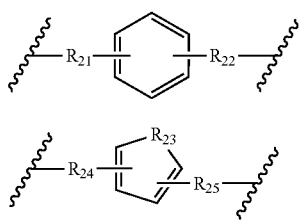

[Chemical Formula 2-2]

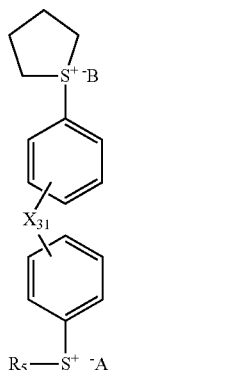

wherein in the formulas (2-1) and (2-2), $R_{21}$, $R_{22}$, $R_{24}$ and $R_{25}$ each independently represent any one selected from the group consisting of a single bond, an alkanediyl group having 1 to 5 carbon atoms, and an alkenediyl group having 2 to 5 carbon atoms; and $R_{23}$ represents any one selected from the group consisting of —O— and —S—.

The electron-donating group may be any one selected from the group consisting of —O—, —S—, —OCH$_2$—, —OCH$_2$O—, —OCH$_2$CH$_2$O—, —O(C$_6$H$_4$)O—, —CH$_2$SCH$_2$—, —S(C$_6$H$_4$)S—, and groups represented by the following formulas (3-1) to (3-3):

[Chemical Formula 3-1]

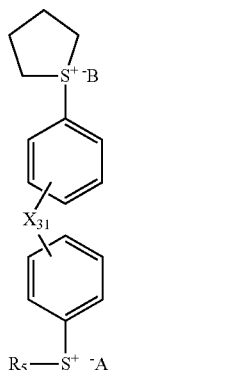

[Chemical Formula 3-2]

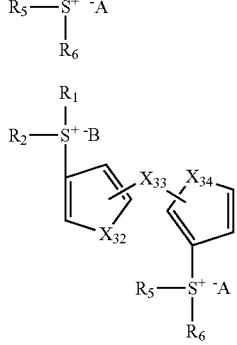

[Chemical Formula 3-3]

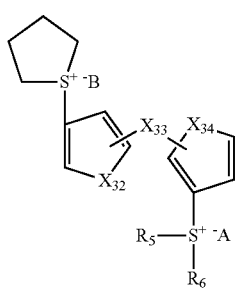

wherein in the formulas (3-1) to (3-3), $X_{31}$ represents any one selected from the group consisting of —O—, —S—, —OCH$_2$—, —OCH$_2$O—, —OCH$_2$CH$_2$O—, —O(C$_6$H$_4$)O—, —CH$_2$SCH$_2$— and —S(C$_6$H$_4$)S—; $X_{32}$ and $X_{34}$ each independently represent any one selected from the group consisting of —O— and —S—; $X_{33}$ represents any one selected from the group consisting of —O—, —S—, —OCH$_2$—, —OCH$_2$O—, —OCH$_2$CH$_2$O—, —CH$_2$SCH$_2$— and —CH$_2$SCH$_2$—; $R_1$ and $R_2$ each independently represent any one selected from the group consisting of an alkyl group, a cycloalkyl group, an aryl group, a heteroalkyl group, a heterocycloalkyl group and a heteroaryl group; $R_5$ and $R_6$ each independently represent any one selected from the group consisting of an alkyl group, a cycloalkyl group, an aryl group, a heteroalkyl group, a heterocycloalkyl group and a heteroaryl group, or $R_5$ and $R_6$ may be joined, together with the sulfur atom to which $R_5$ is bonded, to form a heterocycloalkyl group having 2 to 7 carbon atoms; and $A^-$ and $B^-$ represent anions that are different from each other.

The sulfonium compound described above may be any one selected from the group consisting of compounds represented by the following formulas (4-1) to (4-6):

[Chemical Formula 4-1]

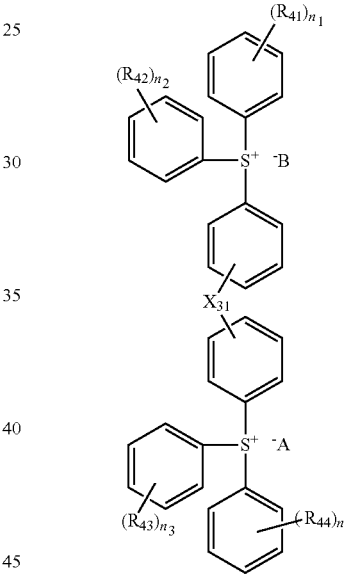

[Chemical Formula 4-2]

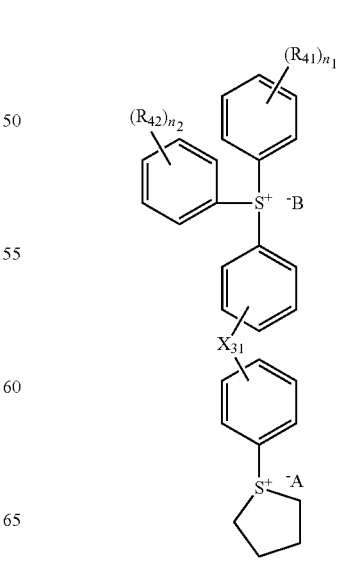

[Chemical Formula 4-3]

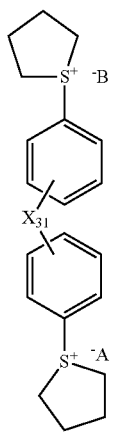

[Chemical Formula 4-4]

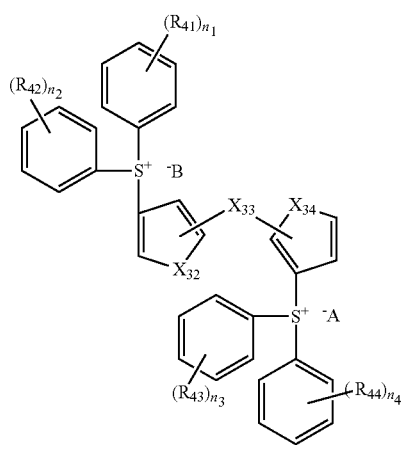

[Chemical Formula 4-5]

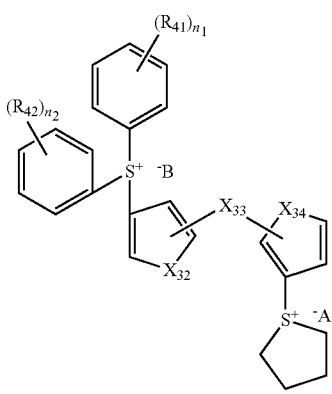

[Chemical Formula 4-6]

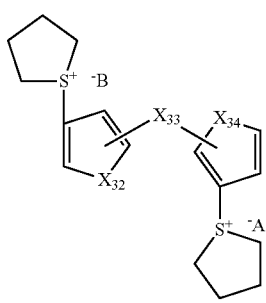

wherein in the formulas (4-1) to (4-6), $X_{31}$ represents any one selected from the group consisting of —O—, —S—, —OCH$_2$—, —OCH$_2$O—, —OCH$_2$CH$_2$O—, —O(C$_6$H$_4$)O—, —CH$_2$SCH$_2$— and —S(C$_6$H$_4$)S—; $X_{32}$ and $X_{34}$ each independently represent any one selected from the group consisting of —O— and —S—; $X_{33}$ represents any one selected from the group consisting of —O—, —S—, —OCH$_2$—, —OCH$_2$O—, —OCH$_2$CH$_2$O— and —CH$_2$SCH$_2$—; $R_{41}$, $R_{42}$, $R_{43}$ and $R_{44}$ each independently represent any one selected from the group consisting of a hydrogen atom, an alkyl group having 1 to 5 carbon atoms, and a halogenated alkyl group having 1 to 5 carbon atoms; $n_1$, $n_2$, $n_3$ and $n_4$ each independently represent an integer from 1 to 5; and A$^-$ and B$^-$ represent anions that are different from each other.

According to another aspect of the present invention, there is provided a photo-acid generator containing the sulfonium compound.

According to another aspect of the present invention, there is provided a method for producing the sulfonium compound described above, which includes a first step of allowing a compound represented by the following formula (10) to react with a compound represented by the following formula (11) and thereby producing a compound represented by the following formula (12); a second step of allowing the compound represented by the formula (12) to react with a compound represented by the following formula (13), and thereby producing a compound represented by the following formula (14); and a third step of allowing a compound represented by the formula (14) to react with a compound represented by the following formula (15), and thereby producing a compound represented by the following formula (1):

[Chemical Formula 10]

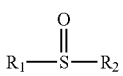

[Chemical Formula 11]

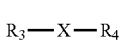

[Chemical Formula 12]

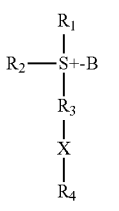

[Chemical Formula 13]

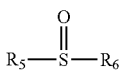

[Chemical Formula 14]

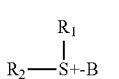

[Chemical Formula 15]

$M^+$_A

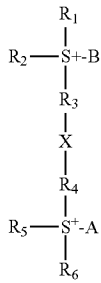

[Chemical Formula 1]

wherein in the formulas (1) and (10) to (15), X represents an electron-donating group; $R_1$ and $R_2$ each independently represent any one selected from the group consisting of an alkyl group, a cycloalkyl group, an aryl group, a heteroalkyl group, a heterocycloalkyl group and a heteroaryl group, or $R_1$ and $R_2$ may be joined, together with the sulfur atom to which $R_1$ is bonded, to form a heterocycloalkyl group having 2 to 7 carbon atoms; $R_3$ and $R_4$ each independently represent any one selected from the group consisting of an arylene group and a heteroarylene group; $R_5$ and $R_6$ each independently represent any one selected from the group consisting of an alkyl group, a cycloalkyl group, an aryl group, a heteroalkyl group, a heterocycloalkyl group and a heteroaryl group, or $R_5$ and $R_6$ may be joined, together with the sulfur atom to which $R_5$ is bonded, to form a heterocycloalkyl group having 2 to 7 carbon atoms; $A^-$ and $B^-$ represent anions that are different from each other; and M represents any one selected from the group consisting of lithium (Li), sodium (Na), potassium (K) and silver (Ag).

DETAILED DESCRIPTION OF THE INVENTION

Hereinafter, the present invention will be described in more detail.

The definitions of the terms used in the present specification are as follows.

The term electron-donating group (EDG) as used herein means a substituent capable of giving an electron.

Unless particularly stated otherwise, the term alkyl group as used herein includes a primary alkyl group, a secondary alkyl group and a tertiary alkyl group.

Unless particularly stated otherwise, the term aryl group as used herein means a hydrocarbon containing one or two or more aromatic groups. Examples thereof include a benzyl group and a naphthyl group.

Unless particularly stated otherwise, the term cycloalkyl group as used herein includes monocyclic, bicyclic, tricyclic and tetracyclic cycloalkyl groups. The term also includes polycyclic cycloalkyl groups including an adamantyl group and a norbornyl group.

Unless particularly stated otherwise, the prefix "hetero-" means that one to three carbon atoms are substituted by heteroatoms selected from the group consisting of —N—, —O—, —S— and —P—. For example, a heteroalkyl group means that one to three carbon atoms among the carbon atoms of the alkyl group are substituted by those heteroatoms.

Unless particularly stated otherwise, the term halogen atom means any one selected from the group consisting of fluorine, chlorine, bromine and iodine.

Unless particularly stated otherwise, all of the compounds and substituents mentioned in the present specification may be substituted or unsubstituted. Here, the term "substituted" means that a hydrogen atom is substituted with any one selected from the group consisting of a halogen atom, a hydroxyl group, a carboxyl group, a cyano group, a nitro group, an amino group, a thio group, a methylthio group, an alkoxy group, a nitrile group, an aldehyde group, an epoxy group, an ether group, an ester group, a carbonyl group, an acetal group, a ketone group, an alkyl group, a cycloalkyl group, a heterocycloalkyl group, an allyl group, a benzyl group, an aryl group, a heteroaryl group, derivatives thereof and combinations thereof.

Unless particularly stated otherwise, the prefix "halogenated" as used herein means that a hydrogen is substituted by any one atom selected from the group consisting of fluorine, chlorine, bromine and iodine.

Unless particularly stated otherwise, the term perfluoroalkyl group as used herein means an alkyl group having a part or all of the hydrogen atoms are substituted by fluorine.

Unless particularly stated otherwise, the term haloalkyl group as used herein means a halogenated alkyl group.

Unless particularly stated otherwise, the term alkylsulfonyl group means a compound containing a sulfonyl group and an alkyl group, or a derivative thereof.

Unless particularly stated otherwise, the term alkanediyl group as used herein is a divalent atomic group obtained by extracting two hydrogen atoms from an alkane, and can be represented by the general formula: $—C_nH_{2n}—$. The term alkenediyl means a divalent atomic group obtained by extracting two hydrogen atoms from an alkene, and can be represented by the general formula: $—C_nH_n—$. The term arylene group means a group obtained by extracting two hydrogen atoms from an aryl group.

Unless particularly stated otherwise in the present specification, an alkyl group means a linear or branched alkyl group having 1 to 30 carbon atoms; a cycloalkyl group means a cycloalkyl group having 3 to 32 carbon atoms; an aryl group means an aryl group having 6 to 30 carbon atoms; a heteroalkyl group means a heteroalkyl group having 1 to 30 carbon atoms; a heterocycloalkyl group means a heterocycloalkyl group having 2 to 32 carbon atoms; a heteroaryl group means a heteroaryl group having 2 to 30 carbon atoms; an arylene group means an arylene group having 6 to 40 carbon atoms; a heteroarylene group means a heteroarylene group having 6 to 40 carbon atoms; an allyl group means an allyl group having 2 to 30 carbon atoms; a perfluoroalkyl group means a perfluoroalkyl group having 1 to 30 carbon atoms; a haloalkyl group means a haloalkyl group having 1 to 30 carbon atoms; and an alkylsulfonyl group means an alkylsulfonyl group having 1 to 30 carbon atoms.

The sulfonium compound according to an embodiment of the present invention is represented by the following formula (1):

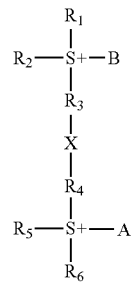

[Chemical Formula 1]

In the formula (1), X represents an electron-donating group; and X is preferably any one selected from the group consisting of —O—, —S—, —OCH$_2$—, —OCH$_2$O—, —OCH$_2$CH$_2$O—, —O(C$_6$H$_4$)O—, —CH$_2$SCH$_2$— and —S(C$_6$H$_4$)S—.

In the formula (1), $R_1$ and $R_2$ each independently represent any one selected from the group consisting of an alkyl group, a cycloalkyl group, an aryl group, a heteroalkyl group, a heterocycloalkyl group and a heteroaryl group, or $R_1$ and $R_2$ may be joined, together with the sulfur atom to which $R^1$ is bonded, to form a heterocycloalkyl group having 2 to 7 carbon atoms.

In the formula (1), $R_5$ and $R_6$ each independently represent any one selected from the group consisting of an alkyl group, a cycloalkyl group, an aryl group, a heteroalkyl group, a heterocycloalkyl group and a heteroaryl group, or $R_5$ and $R_6$ may be joined, together with the sulfur atom to which $R_5$ is bonded, to form a heterocycloalkyl group having 2 to 7 carbon atoms.

In the formula (1), $R_3$ and $R_4$ each independently represent any one selected from the group consisting of an arylene group and a heteroarylene group.

In the formula (1), $R_3$ and $R_4$ each independently represent any one selected from the group consisting of the following formulas (2-1) and (2-2):

[Chemical Formula 2-1]

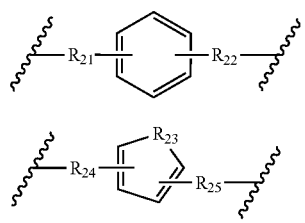

[Chemical Formula 2-2]

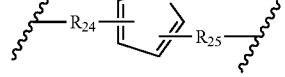

In the formula (2-1) and formula (2-2), $R_{21}$, $R_{22}$, $R_{24}$ and $R_{25}$ each independently represent any one selected from the group consisting of a single bond, an alkanediyl group having 1 to 5 carbon atoms, and an alkenediyl group having 2 to 5 carbon atoms; and $R_{23}$ represents any one selected from the group consisting of —O— and —S—.

In the formula (1), $A^-$ and $B^-$ are anions that are different from each other.

The anions $A^-$ and $B^-$ each represent any one selected from the group consisting of a sulfonate anion, an imide anion, a methide anion, an alkyl halide anion, a carboxylate anion, an iodonium anion and a sulfonylimide anion.

$A^-$ and $B^-$ may each independently represent any one selected from the group consisting of the following formulas (1-1), (1-2) and (1-3):

[Chemical Formula 1-1]

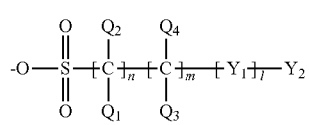

wherein in the formula (1-1), $Q_1$, $Q_2$, $Q_3$ and $Q_4$ each represent any one selected from the group consisting of a hydrogen atom, a halogen atom, and an alkyl group; $Y_1$ represents any one selected from the group consisting of an alkanediyl group, an alkenediyl group, NR', S, O, CO and combinations thereof; R' represents any one selected from the group consisting of a hydrogen atom and an alkyl group; $Y_2$ represents any one selected from the group consisting of a hydrogen atom, an alkyl group, a heterocycloalkyl group, an aryl group, a heteroaryl group, an alkyl group, a heteroalkyl group, an allyl group, a perfluoroalkyl group, a haloalkyl group and an alkylsulfonyl group; n represents an integer from 0 to 10; m represents an integer from 0 to 10; and l represents an integer from 0 to 5;

[Chemical Formula 1-2]

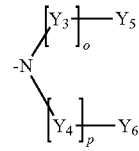

wherein in the formula (1-2), $Y_3$ and $Y_4$ each independently represent any one selected from the group consisting of an alkanediyl group, an alkenediyl group, NR', S, O, CO, O$_2$S and combinations thereof; R' represents any one selected from the group consisting of a hydrogen atom and an alkyl group; $Y_5$ and $Y_6$ each independently represent any one selected from the group consisting of a hydrogen atom, an alkyl group, a heterocycloalkyl group, an aryl group, a heteroaryl group, an alkyl group, a heteroalkyl group, an allyl group, a perfluoroalkyl group, a haloalkyl group and an alkylsulfonyl group; o represents an integer from 0 to 5; and p represents an integer from 0 to 5;

[Chemical Formula 1-3]

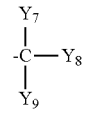

wherein in the formula (1-3), $Y_7$, $Y_8$ and $Y_9$ each independently represent any one selected from the group consisting of a hydrogen atom, an alkyl group, a heterocycloalkyl group, an aryl group, a heteroaryl group, an alkyl group, a heteroalkyl group, an allyl group, a perfluoroalkyl group, a haloalkyl group, and an alkylsulfnoyl group.

Preferably, the anions $A^-$ and $B^-$ may each independently represent any one selected from the group consisting of $^-OSO_2CF_3$, $^-OSO_2C_4F_9$, $^-OSO_2C_8F_{17}$, $^-N(CF_3)_2$, $^-N(C_2F_5)_2$, $^-N(C_4F_9)_2$, $^-C(CF_3)_3$, $^-C(C_2F_5)_3$, $^-C(C_4F_9)_3$ and an anionic moiety represented by the following formula (1-4):

[Chemical Formula 1-4]

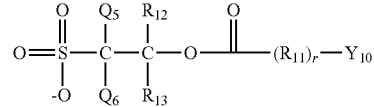

wherein in the formula (1-4), $Y_{10}$ represents any one selected from the group consisting of a cycloalkyl group, a heterocycloalkyl group, an aryl group, a heteroaryl group, an alkyl group, a heteroalkyl group, an allyl group, a perfluoroalkyl group, a haloalkyl group, and an alkylsulfonyl group; $R_{11}$ represents any one selected from the group consisting of an alkanediyl group, an alkenediyl group, NR', S, O, CO and combinations thereof; R' represents any one selected from the group consisting of a hydrogen atom and an alkyl group; $R_{12}$ and $R_{13}$ each independently represent any one selected from the group consisting of a hydrogen atom and an alkyl group having 1 to 9 carbon atoms; r represents an integer from 0 to 5; and $Q_5$ and $Q_6$ each independently represent a halogen atom.

The anions A− and B− are different from each other, and A− may be any one selected from the group consisting of $OSO_2CF_3^-$, $OSO_2CF_2CF_2CF_3^-$ and an anionic moiety represented by the following formula (1-5), while B− may be any one selected from the group consisting of $OSO_2CF_3^-$, $OSO_2CF_2CF_2CF_3^-$ and an anionic moiety represented by the following formula (1-5). In this case, the line width roughness can be reduced, and as compared with the conventional practice of using a mixture of anions having high diffusion properties and low diffusion properties, compatibility or the complicatedness of the production process can be decreased.

[Chemical Formula 1-5]

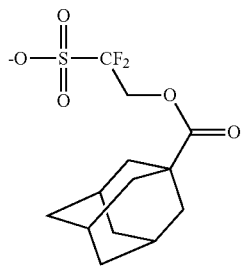

The compound represented by the formula (1) can be used as a photo-acid generator, and when the compound represented by the formula (1) is used as a photo-acid generator, two molecules of acid that is generated at the time of light irradiation are generated simultaneously from one molecule, so that when acid generators having fast and slow diffusion rates, and acid generators having high and low permeabilities are to be applied simultaneously, the complicatedness of using a mixture of two kinds of acid generators can be reduced. Furthermore, a photo-acid generator which can solve the problem of uniform compatibility of in the resist, which occurs when two kinds of conventional acid generators are used in mixture, and can enhance the line edge roughness (LER), sensitivity and resolution, which are the pattern characteristics of a resist, can be provided.

The sulfonium compound represented by the formula (1) may be any one selected from the group consisting of compounds represented by the following formula (3-1), formula (3-2) and formula (3-3):

[Chemical Formula 3-1]

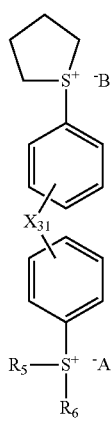

[Chemical Formula 3-2]

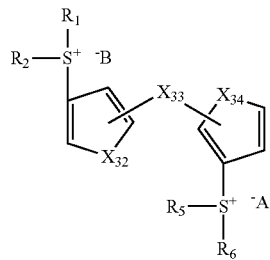

[Chemical Formula 3-3]

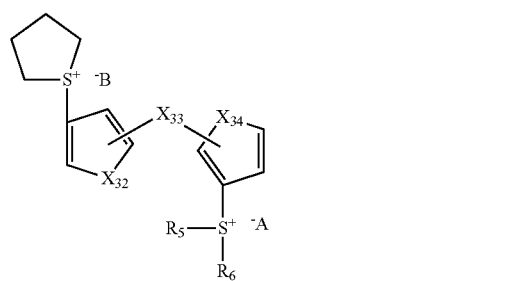

wherein in the formulas (3-1) to (3-3), $X_{31}$ represents any one selected from the group consisting of —O—, —S—, —OCH$_2$—, —OCH$_2$O—, —OCH$_2$CH$_2$O—, —O(C$_6$H$_4$)O—, —CH$_2$SCH$_2$— and —S(C$_6$H$_4$)S—; $X_{32}$ and $X_{34}$ each independently represent any one selected from the group consisting of —O— and —S—; $X_{33}$ represents any one selected from the group consisting of —O—, —S—, —OCH$_2$—, —OCH$_2$O—, —OCH$_2$CH$_2$O—, —CH$_2$SCH$_2$— and —CH$_2$SCH$_2$—; $R_1$ and $R_2$ each independently represent any one selected from the group consisting of an alkyl group, a cycloalkyl group, an aryl group, a heteroalkyl group, a heterocycloalkyl group and a heteroaryl group; $R_5$ and $R_6$ each independently represent any one selected from the group consisting of an alkyl group, a cycloalkyl group, an aryl group, a heteroaryl group, a heterocycloalkyl group and a heteroaryl group, or $R_5$ and $R_6$ may be joined, together with the sulfur atom to which $R_5$ is bonded, to form a heterocycloalkyl group having 2 to 7 carbon atoms; and A⁻ and B⁻ are anions that are different from each other.

The anions A⁻ and B⁻ have the same meanings as defined in connection with the formula (1), and further descriptions thereof will not be repeated here.

The sulfonium compound may be any one selected from the group consisting of compounds represented by the following formulas (4-1) to (4-6):

[Chemical Formula 4-1]

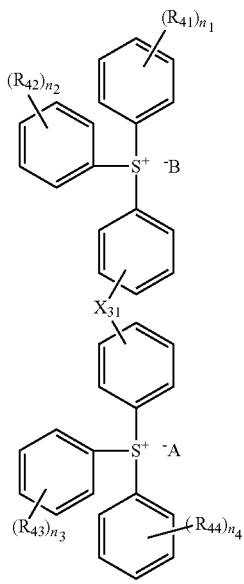

[Chemical Formula 4-2]

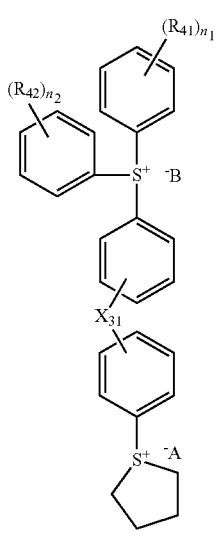

[Chemical Formula 4-3]

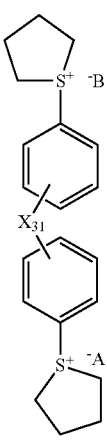

[Chemical Formula 4-4]

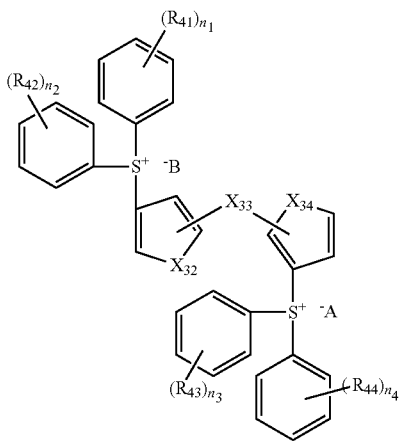

[Chemical Formula 4-5]

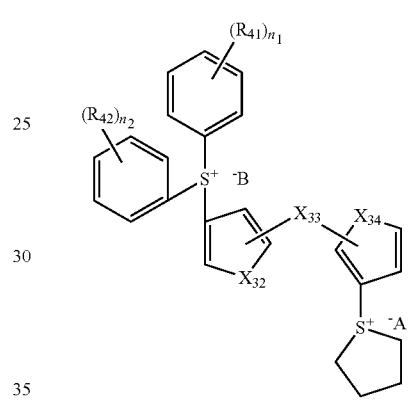

[Chemical Formula 4-6]

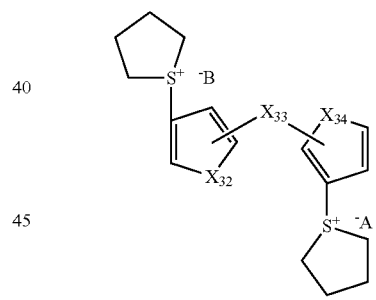

wherein in the formulas (4-1) to (4-6), $X_{31}$ represents any one selected from the group consisting of —O—, —S—, —OCH$_2$—, —OCH$_2$O—, —OCH$_2$CH$_2$O—, —O(C$_6$H$_4$)O—, —CH$_2$SCH$_2$— and —S(C$_6$H$_4$)S—; $X_{32}$ and $X_{34}$ each independently represent any one selected from the group consisting of —O— and —S—; $X_{33}$ represents any one selected from the group consisting of —O—, —S—, —OCH$_2$—, —OCH$_2$O—, —OCH$_2$CH$_2$O— and —CH$_2$SCH$_2$—; $R_{41}$, $R_{42}$, $R_{43}$ and $R_{44}$ each independently represent any one selected from the group consisting of a hydrogen atom, an alkyl group having 1 to 5 carbon atoms, and a halogenated alkyl group having 1 to 5 carbon atoms; $n_1$, $n_2$, $n_3$ and $n_4$ each independently represent an integer from 1 to 5; and A$^-$ and B$^-$ are anions that are different from each other.

The anions A$^-$ and B$^-$ have the same meanings as defined in connection with the formula (1), and further descriptions thereof will not be repeated here.

The sulfonium compound may be any one selected from the group consisting of compounds represented by the following formulas (51) to (5-14):
[Chemical Formula 5-1]
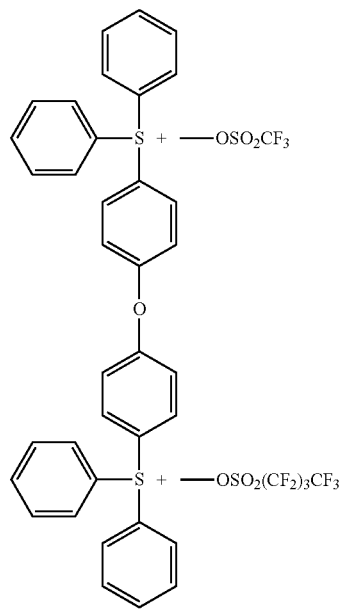
[Chemical Formula 5-2]
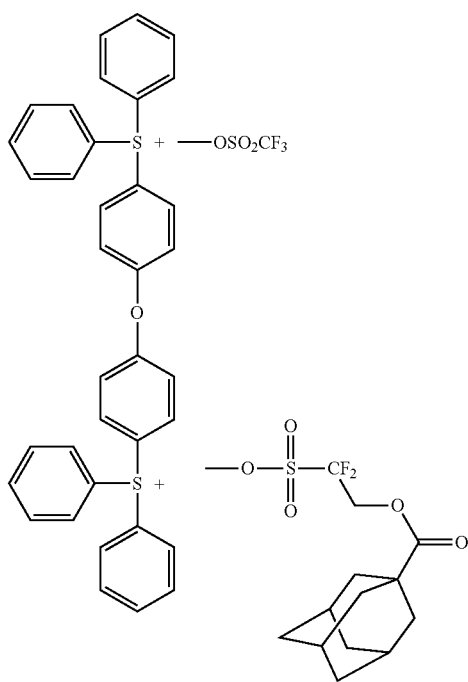
[Chemical Formula 5-3]
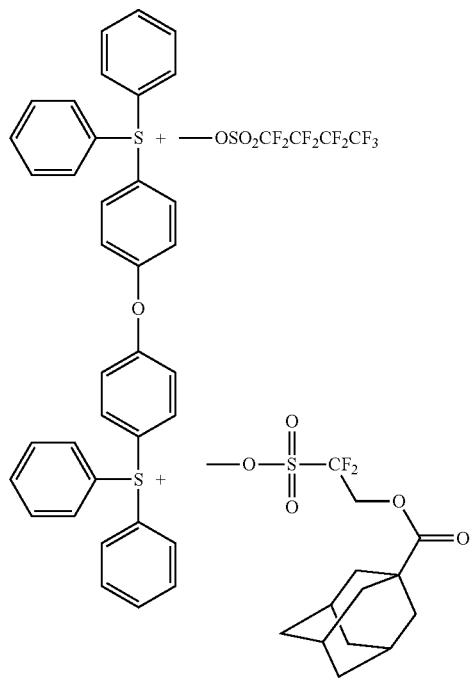
[Chemical Formula 5-4]
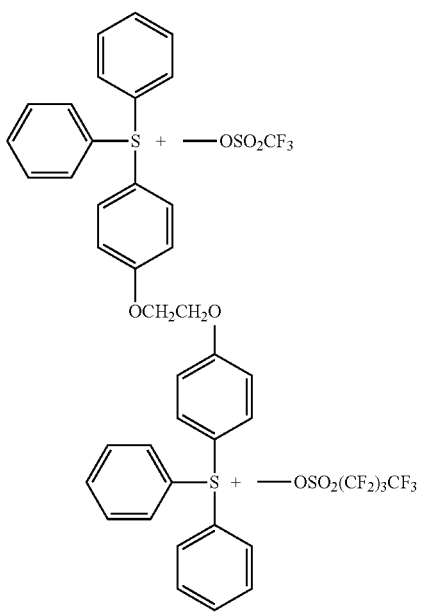

[Chemical Formula 5-5]
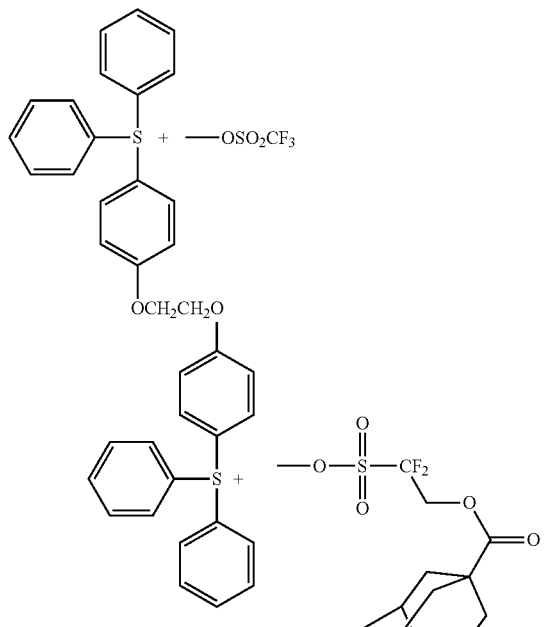
[Chemical Formula 5-6]
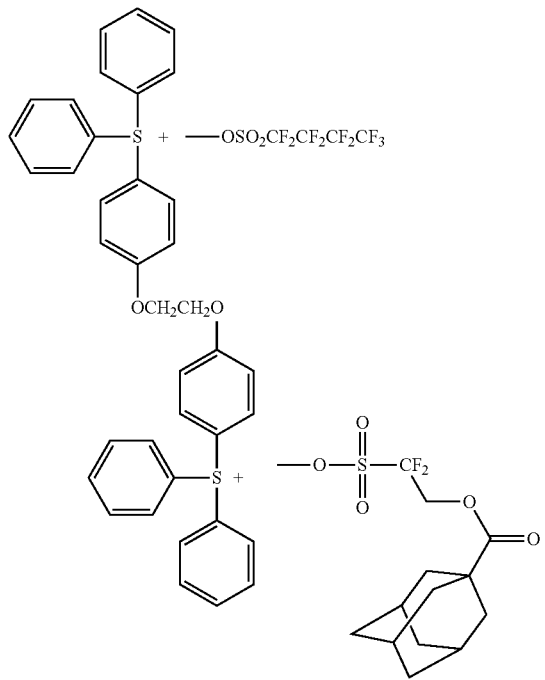
[Chemical Formula 5-7]
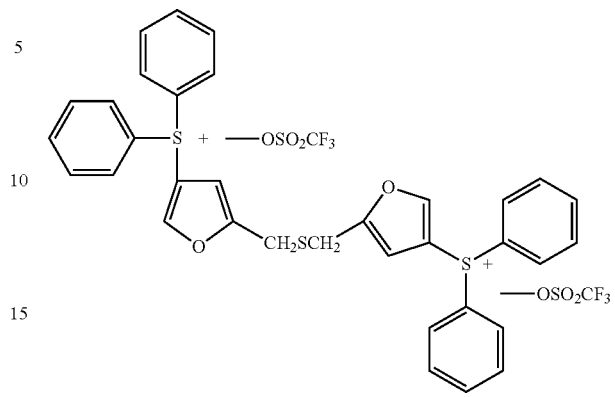
[Chemical Formula 5-8]
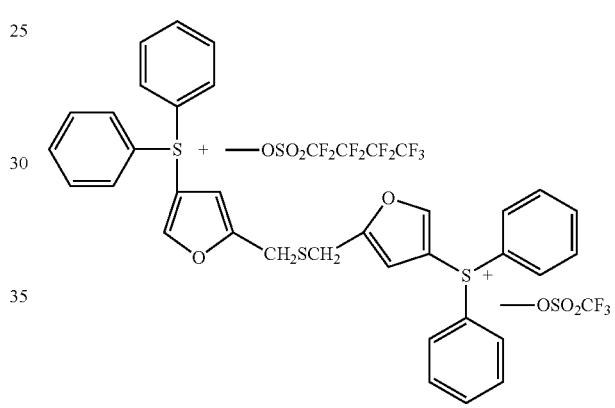
[Chemical Formula 5-9]
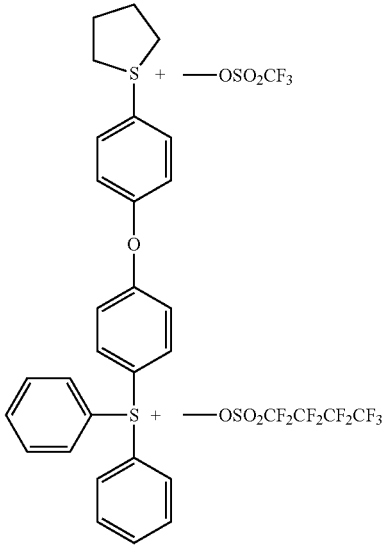

[Chemical Formula 5-10]
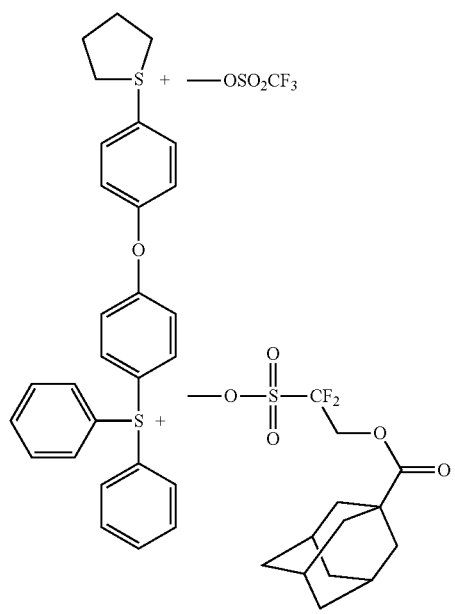
[Chemical Formula 5-11]
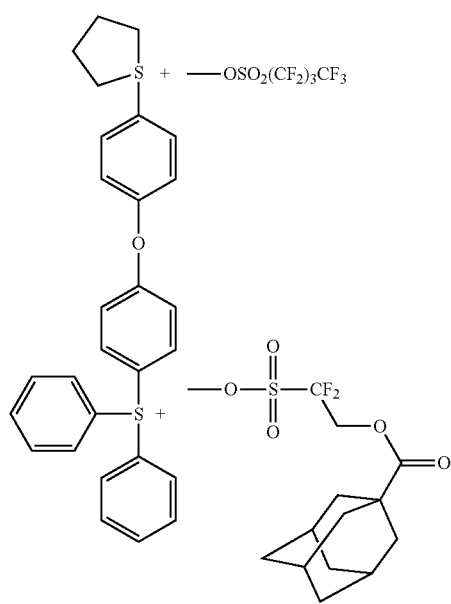
[Chemical Formula 5-12]
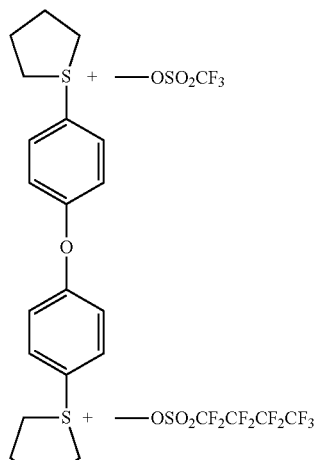
[Chemical Formula 5-13]
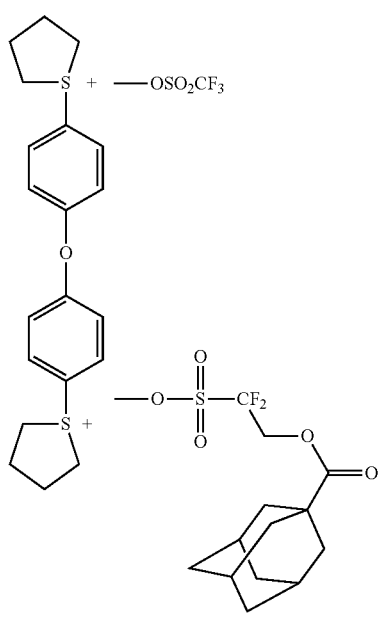

[Chemical Formula 5-14]

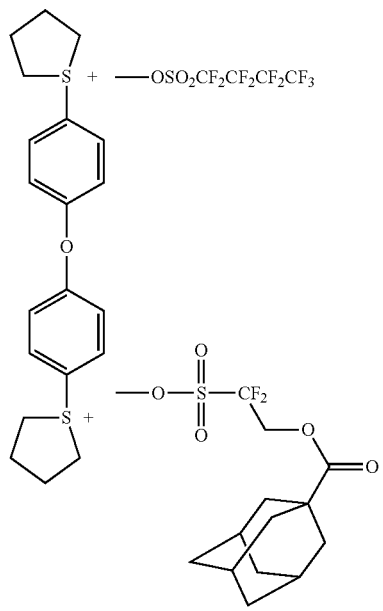

The photo-acid generator according to another embodiment of the present invention contains the sulfonium compound represented by the formula (1).

The descriptions on the sulfonium compound are substantially the same as given above, and further descriptions thereon will not be repeated here.

The sulfonium compound of the present invention is such that two different acid molecules are generated from one molecule of the sulfonium compound. Thus, the inconvenience of using a mixture of photo-acid generators having different properties can be addressed, and the problem of uniform compatibility in the resist is also solved. Thus, an excellent resist pattern can be obtained.

The method for producing a sulfonium compound according to another embodiment of the present invention includes a first step of allowing a compound represented by the following formula (10) to react with a compound represented by the following formula (11), and thereby producing a compound represented by the following formula (12); a second step of allowing a compound represented by the following formula (12) to react with a compound represented by the following formula (13), and thereby producing a compound represented by the following formula (14); and a third step of allowing a compound represented by the following formula (14) to react with a compound represented by the following formula (15), and thereby producing a compound represented by the following formula (1):

[Chemical Formula 10]

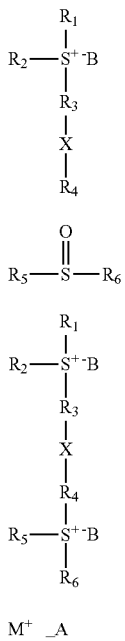

[Chemical Formula 11]

$R_3 — X — R_4$

[Chemical Formula 12]

[Chemical Formula 13]

$$R_5 — \overset{\overset{O}{\|}}{S} — R_6$$

[Chemical Formula 14]

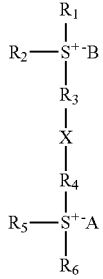

[Chemical Formula 15]

$M^+ \_A^-$

[Chemical Formula 1]

wherein in the formulas (1) and (10) to (15), X, $R_1$, $R_2$, $R_3$, $R_4$, $R_5$, $R_6$, $A^-$ and $B^-$ have the same meanings as defined above in connection with the sulfonium compound represented by the formula (1), and further descriptions thereon will not be repeated here.

In the formula (15), M represents any one selected from the group consisting of Li, Na, K and Ag.

The first step includes a process of mixing the compound represented by the formula (11) and the compound represented by the formula (12) to prepare a reaction mixture liquid; a process of adding triflic anhydride dropwise to the reaction mixture liquid to prepare a reaction mixture liquid; and a process of allowing the reaction mixture liquid to react for 30 minutes to 6 hours while maintaining the temperature at −80° C. to −10° C.

The respective processes in the step can be carried out in a reaction solvent, and any non-aqueous solvent can be applied as the reaction solvent. Preferred examples of the reaction solvent include dichloromethane (MC), chloroform (CHCl$_3$), acetonitrile, ethylene carbonate (EC), propylene carbonate (PC), butylene carbonate, dimethylvinylene carbonate, vinylethylene carbonate, methyl ethyl carbonate (MEC), methyl propyl carbonate, methyl butyl carbonate, ethyl propyl carbonate, dimethyl carbonate (DMC), diethyl carbonate (DEC), dipropyl carbonate, dibutyl carbonate methyl propionate, methyl pivalate, butyl pivalate, hexyl pivalate, octyl pivalate, dimethyl oxalate, ethyl methyl oxalate, diethyl oxalate, tetrahydrofuran, 2-methyltetrahydrofuran, 1,4-dioxane, 1,2-dimethoxyethane, 1,2-diethoxyethane, 1,2-dibutoxyethane, dimethylformamide, trimethyl phosphate, tributyl phosphate, trioctyl phosphate, divinylsulfone, adiponitrile, 1,4-propanesultone, 1,4-butanediol, dimethane sulfonate, propylene sulfite, glycol sulfate, propylene sulfate, dipropargyl sulfite, methyl propargyl sulfite, ethyl propargyl sulfite, 1,4-butanediol dimethane sulfonate, propylene sulfite, glycol sulfate, propylene sulfate, methyl ethyl ketone, and combinations thereof.

The second step specifically includes a process of mixing the compound represented by the formula (12) and the compound represented by the formula (13) to prepare a reaction solution, and allowing the reaction solution to react while stirring the reaction solution for 30 minutes to 3 hours at 15° C. to 30° C.

The third step includes a process of mixing the compound represented by the formula (14) with the reaction solvent to prepare a solution, dissolving the compound represented by the formula (15) in distilled water, mixing the resulting solution with the previously prepared solution, and allowing the mixture to react while stirring the mixture for 30 minutes to 5 hours at 15° C. to 30° C.

The respective steps can further include purification processes, and there are no particular limitations on the purification processes to be applied, as long as they are methods for concentrating and purifying the reaction products.

The method for producing a sulfonium compound is simple, and can produce a sulfonium compound having two acid sites, with a high yield.

The sulfonium compound of the present invention can generate two different acid molecules from one molecule. Thus, the inconvenience of using a mixture of different acid generators occurring in the case of using a photo-acid generator can be addressed, uniform compatibility in the resist can be obtained, and when the sulfonium compound is used as a photo-acid generator, a uniform and excellent resist pattern can be obtained.

EXAMPLES

Hereinafter, the present invention will be described in detail by way of Examples so that those having ordinary skill in the art to which the present invention is pertained can easily carry out the invention. However, the present invention can be realized in various different embodiments, and is not intended to be limited to the Examples described herein.

Synthesis Example 1

1) 20 g of diphenyl(diphenyl ether)sulfonium triflate (compound A in the following reaction scheme 1) and 0.8 g of phenyl sulfoxide (compound B in the following reaction scheme 2) were mixed in a flask, and thus a reaction mixture liquid was prepared.

The flask containing the reaction mixture liquid was placed in a bath containing dry ice and acetone, and thus the temperature of the content of the flask was lowered.

When the temperature of the dry ice bath reached −40° C., 10 ml of triflic anhydride (compound C in the following reaction scheme 1) was slowly added dropwise to the flask to prepare a reaction solution.

After completion of the dropwise addition, while the temperature of the reactor was maintained at about −40° C., the reaction was carried out for 2 hours. The completion point of the reaction was checked by thin layer chromatography (TLC), and when it was confirmed that the reaction was completed, the reaction solution was neutralized with an aqueous solution of $K_2CO_3$ to make the reaction solution alkaline.

The alkaline reaction solution was washed two times with distilled water, and then the solvent was evaporated under reduced pressure. The resulting crude reaction liquid concentrate was purified using dichloromethane and hexane, and thus a purified reaction liquid concentrate was obtained.

Di(triphenylsulfonium triflate) ether (compound D in the following reaction scheme 1) was obtained from the purified reaction liquid concentrate, as a white solid in an amount of 30 g (yield: 90%).

$^1$H-NMR (CDCl$_3$-d1): δ(ppm) 7.6-7.9 (m, 24H), 7.4 (d, 4H), $^{19}$F NMR −78(s. 6F)

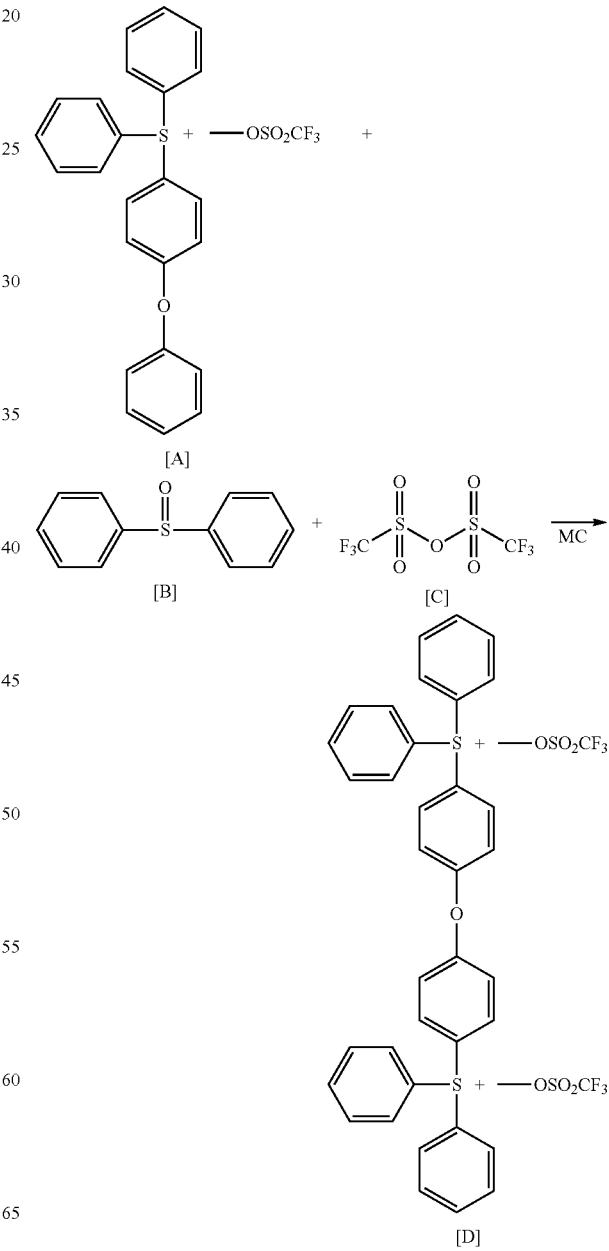

[Reaction Scheme 1]

2) A solution was prepared by dissolving 10 g of di(triphenylsulfonium triflate) ether (compound A in the following reaction scheme 2) synthesized as described above in dichloromethane in a flask, was provided, and then 4.4 g of nonafluorobutane sulfonic acid sodium salt (compound B in the following reaction scheme 2) dissolved in distilled water was introduced into the above-prepared solution. The reaction solution thus prepared was allowed to react for 3 hours at normal temperature under stirring.

The completion point of the reaction was checked by $^{19}$F-NMR, and after the reaction was completed, the reaction liquid was washed two times with distilled water, and then was distilled under reduced pressure to remove the solvent. The reaction product was solidified using dichloromethane and hexane. Thus, 10.2 g of triphenylsulfonium triflate (triphenylsulfonium nonaflate) ether (compound C in the following reaction scheme 2) was obtained from the solidified reaction product (white solid, yield: 87%).

$^1$H-NMR (CDCl3-d1): δ(ppm) 7.6-7.8 (m, 24H), 7.4 (d, 4H), $^{19}$F NMR −78(s. 6F), −81(s. 3F), −114(s, 2F), −121(s, 2F), −126(s, 2F)

[Reaction Scheme 2]

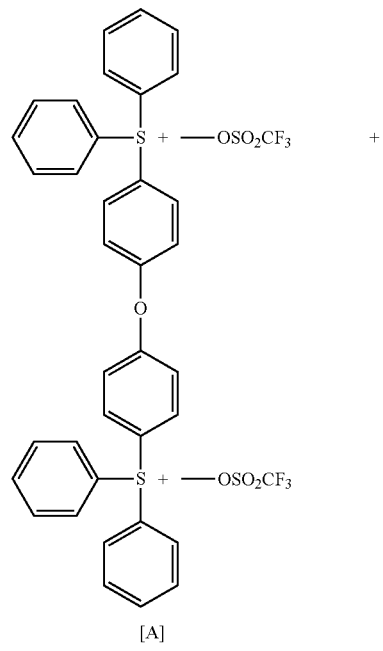

[A]

Na + ——OSO$_2$(CF$_2$)$_3$CF$_3$        $\xrightarrow{MC}$

[B]

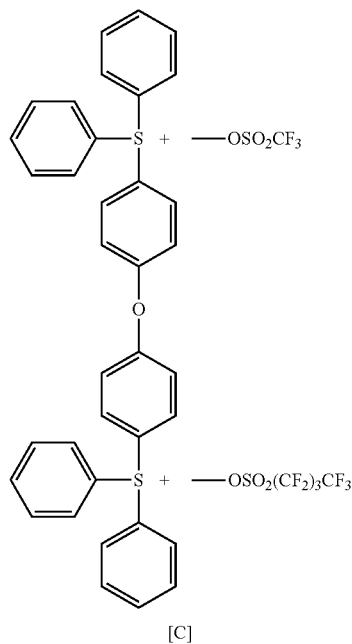

[C]

Synthesis Example 2

10 g of di(triphenylsulfonium triflate) ether (compound A in the following reaction scheme 3) produced in Synthesis Example 1-1) was placed in a flask and was dissolved in dichloromethane. Subsequently, 1.9 g of adamantane-1-carboxylic acid-2,2-difluoro-2-sulfoethyl ester sodium salt (compound B in the following reaction scheme 3) dissolved in distilled water was introduced into the above-prepared solution to prepare a reaction solution.

The reaction solution was stirred for 3 hours at normal temperature (25° C.). The reaction completion point of the reaction solution was checked by $^{19}$F-NMR. The reaction solution thus obtained was washed two times with distilled water and then was distilled under reduced pressure to remove the solvent. The reaction product was solidified using dichloromethane and hexane.

Thus, diphenyl[(diphenyl diphenyl ether)sulfonium triflate](adamantane-1-carboxylic acid-2,2-difluoro-2-sulfoethyl ester)sulfonium salt (compound C in the following reaction scheme 3) was obtained from the solidified reaction product, as a white solid in an amount of 9.5 g (yield: 93%).

$^1$H-NMR (CDCl3-d1): δ(ppm) 1.6~2.0(d, 15H), 4.6~4.8(t, 2H), 7.6~7.9(m, 24H), 7.4 (d, 4H), $^{19}$F NMR −78(s. 3F), −114(s, 2F)

[Reaction Scheme 3]

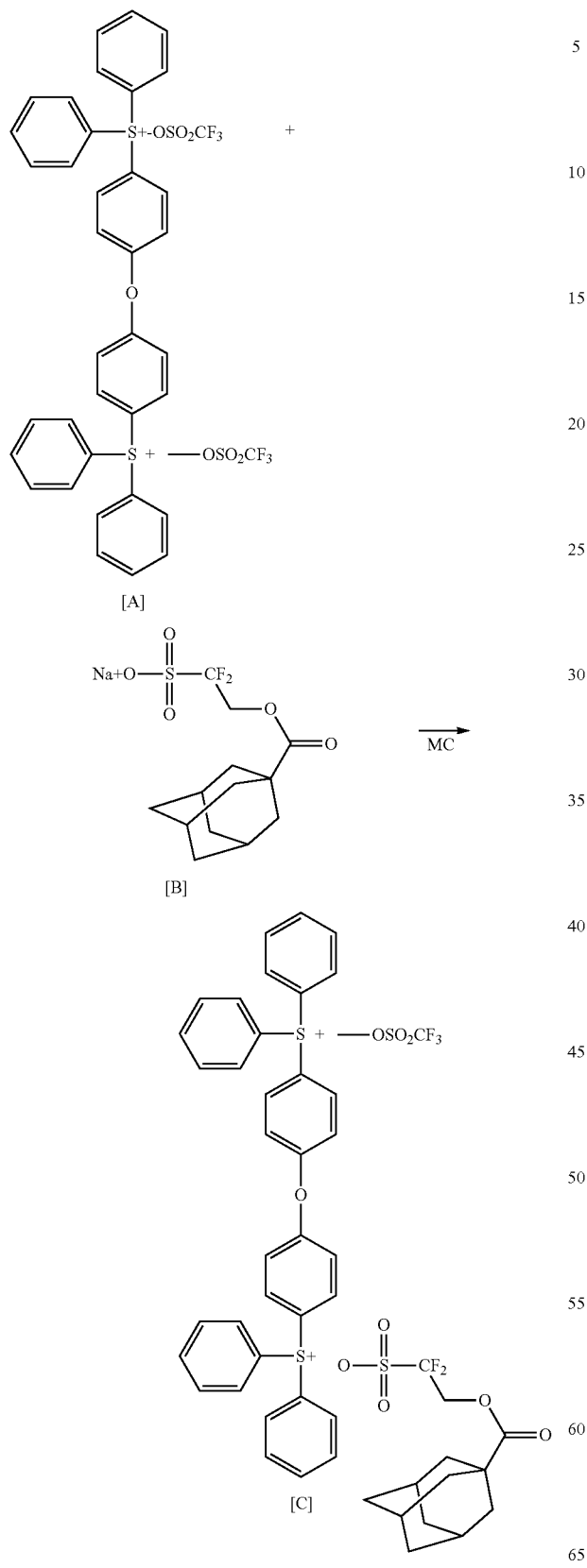

Synthesis Example 3

1) 10 g (49.4 mmol) of phenyl sulfoxide (compound A in the following reaction scheme 4) and 12.95 g (49.4 mmol) of 1,2-diphenoxyethane (compound B in the following reaction scheme 4) were dissolved in dichloromethane in a flask, and thus a reaction mixture liquid was prepared.

The flask containing the reaction mixture liquid was placed in a bath containing dry ice and acetone, and thus the temperature of the content of the flask was lowered.

When the temperature of the dry ice bath reached −40° C., 21 ml of triflic anhydride (compound C in the following reaction scheme 4) was slowly added dropwise to the flask to prepare a reaction solution.

After completion of the dropwise addition, while the temperature of the reactor was maintained at about −40° C., the reaction was carried out for 2 hours. The completion point of the reaction was checked by thin layer chromatography (TLC), and when it was confirmed that the reaction was completed, the reaction solution was neutralized with an aqueous solution of $K_2CO_3$ to make the reaction solution alkaline.

The alkaline reaction solution was washed two times with distilled water, and then the solvent was evaporated under reduced pressure. The resulting crude reaction liquid concentrate was purified using dichloromethane and hexane, and thus a purified reaction liquid concentrate was obtained.

Diphenyl(diphenoxyethane)sulfonium triflate (compound D in the following reaction scheme 4) was obtained from the purified reaction liquid concentrate, in an amount of 18.5 g (yield: 68%).

[Reaction Scheme 4]

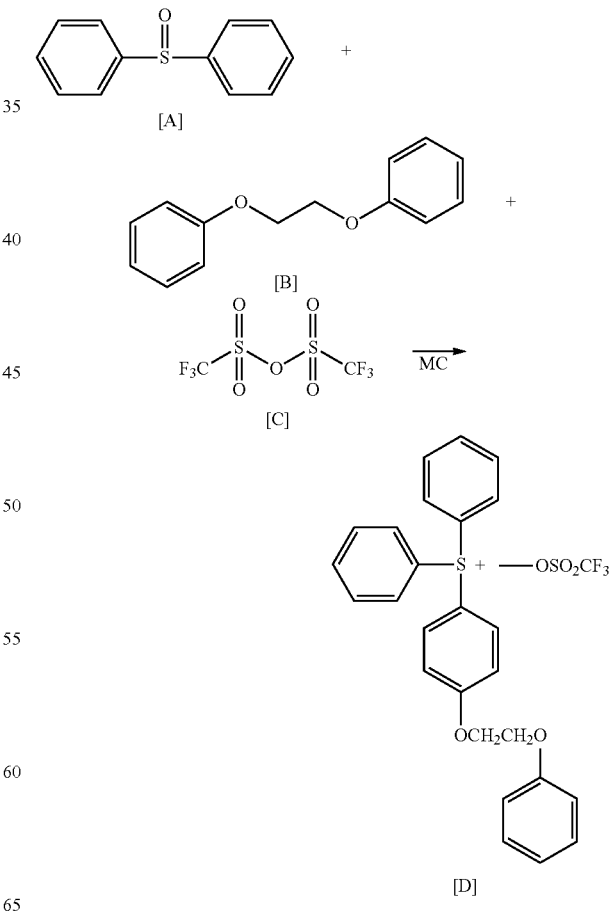

2) The reaction was carried out in the same manner as in Synthesis Example 3-1), except that a reaction mixture liquid was prepared by dissolving 10 g (18.2 mmol) of diphenyl (diphenoxyethane)sulfonium triflate (compound A in the following reaction scheme 5) 3.68 g (18.2 mmol) of phenyl sulfoxide (compound B in the following reaction scheme 5) in dichloromethane in a flask.

Diphenyl[(diphenyldiphenoxyethane)sulfonium triflate] sulfonium triflate (compound C in the following reaction scheme 5) was obtained from the purified reaction liquid concentrate, in an amount of 11 g (white solid, yield: 68%).

3) 10 g (11.3 mmol) of the diphenyl(methoxyphenyl)sulfonium triflate dimer (compound A in the reaction scheme 6) produced in Synthesis Example 3-2) was placed in a flask and was dissolved in dichloromethane. Subsequently, 3.6 g of nonafluorobutane sulfonic acid sodium salt (compound B in the following reaction scheme 6) dissolved in distilled water was introduced into the above-prepared solution, and thus a reaction mixture liquid was prepared.

The reaction mixture liquid was allowed to react for 3 hours at normal temperature (25° C.) under stirring, and the completion point of the reaction was checked by $^{19}$F-NMR.

The reaction solution thus obtained was washed two or more times with distilled water and then was distilled under reduced pressure to remove the solvent. The reaction solution was solidified using dichloromethane and hexane. Diphenyl [(diphenyldiphenoxyethane)sulfonium triflate]sulfonium nonaflate (compound C in the following reaction scheme 6) was obtained from the solidified reaction product, as a white solid in an amount of 9.2 g (yield: 79%).

$^{1}$H-NMR (DNSO-d6): (ppm) 4.5 (s, 4H), 7.2 (d, 4H), 7.8 (m, 24H)

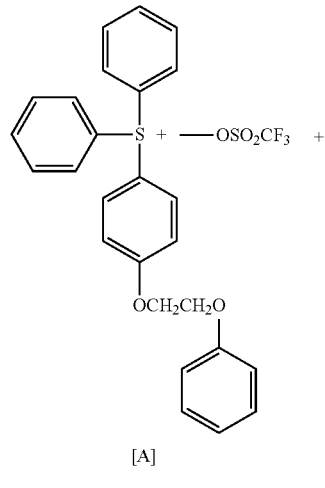

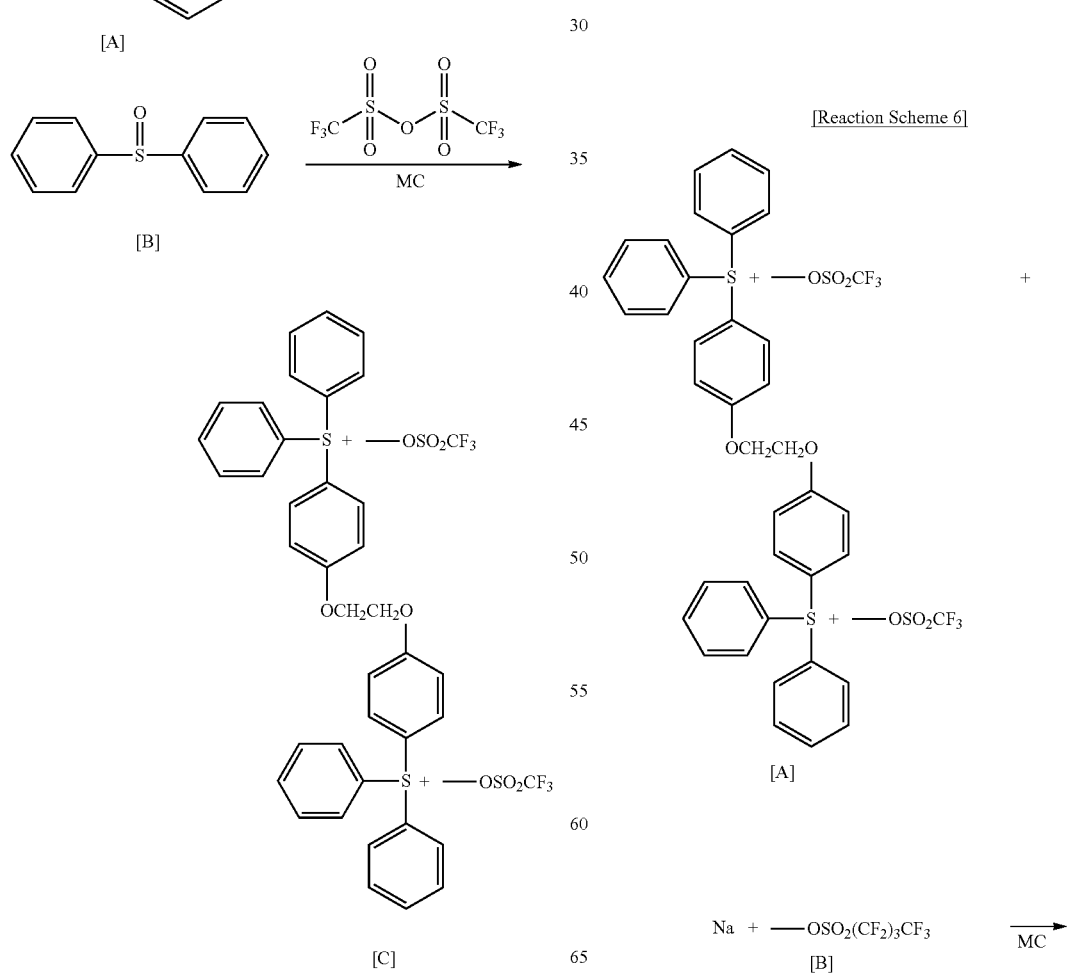

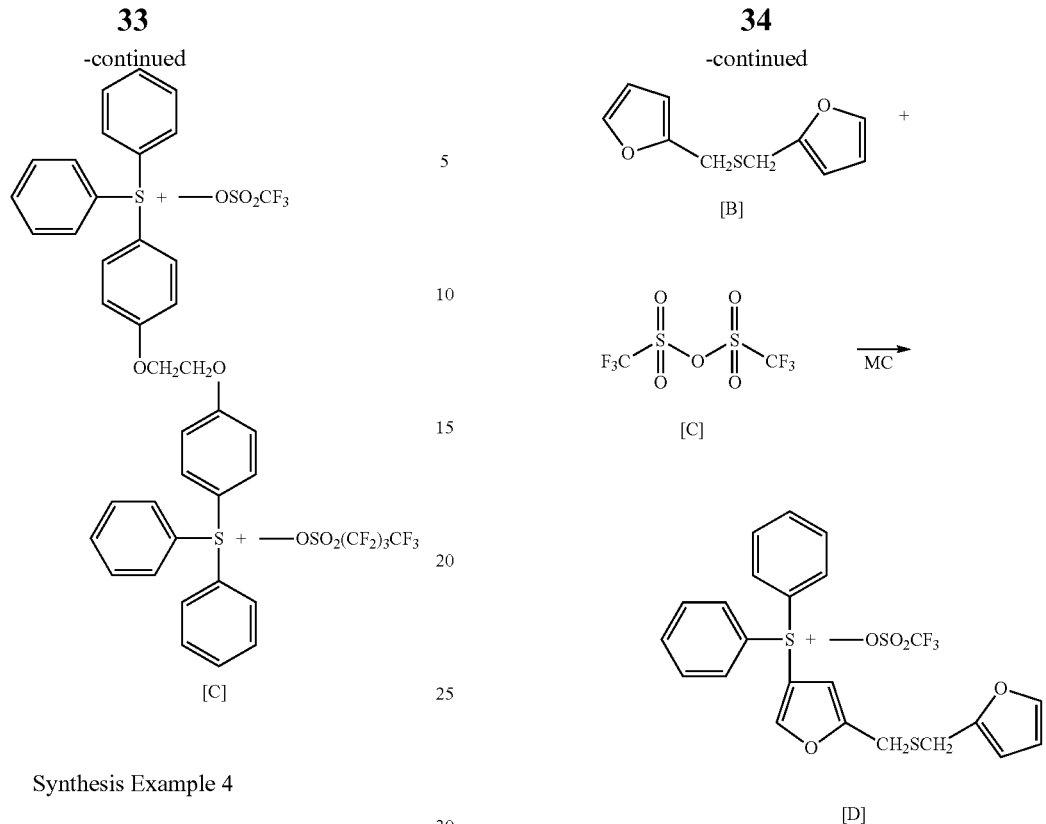

Synthesis Example 4

1) 10 g (49.4 mmol) of phenyl sulfoxide (compound A in the following reaction scheme 7) and 9.6 g (49.4 mmol) of furfuryl sulfide (compound B in the following reaction scheme 7) were dissolved in dichloromethane in a flask, and thus a reaction mixture liquid was prepared.

The flask containing the reaction mixture liquid was placed in a bath containing dry ice and acetone, and thus the temperature of the content of the flask was lowered.

When the temperature of the dry ice bath reached −40° C., 21 ml of triflic anhydride (compound C in the following reaction scheme 7) was slowly added dropwise to the flask to prepare a reaction solution.

After completion of the dropwise addition, while the temperature of the reactor was maintained at about −40° C., the reaction was carried out for 2 hours. The completion point of the reaction was checked by TLC, and when it was confirmed that the reaction was completed, the reaction solution was neutralized with an aqueous solution of $K_2CO_3$ to make the reaction solution alkaline.

The alkaline reaction solution was washed two times with distilled water, and then the solvent was evaporated under reduced pressure. The resulting crude reaction liquid concentrate was purified using dichloromethane and hexane, and thus a purified reaction liquid concentrate was obtained.

Diphenyl[(furfurylsulfidyl)sulfonium triflate] (compound D in the following reaction scheme 7) was obtained from the purified reaction liquid concentrate, in an amount of 15 g (yield: 57%).

2) The reaction was carried out in the same manner as in Synthesis Example 4-1), except that a reaction mixture liquid was prepared by dissolving 10 g (18.9, mmol) of diphenyl [(furfurylsulfidyl)sulfonium triflate] (compound A in the following reaction scheme 8) produced in Synthesis Example 4-1) and 3.7 g (18.9 mmol) of phenyl sulfoxide (compound B in the following reaction scheme 8) in dichloromethane in a flask.

From the above reaction, 10.5 g (yield: 59%) of diphenyl [(diphenylfurfurylsulfidyl)sulfonium triflate]sulfonium triflate (compound C in the following reaction scheme 8) was obtained as a white solid.

[Reaction Scheme 8]

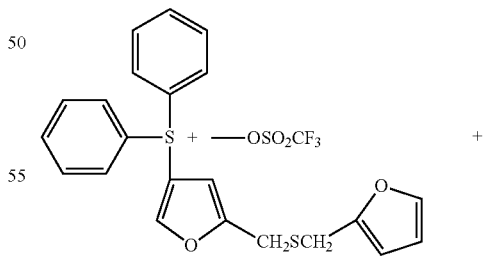

[Reaction Scheme 7]

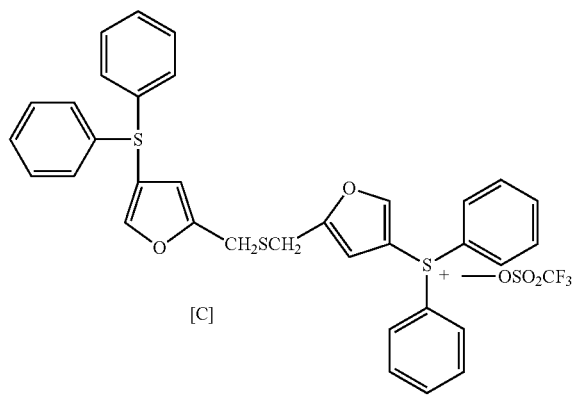

[C]

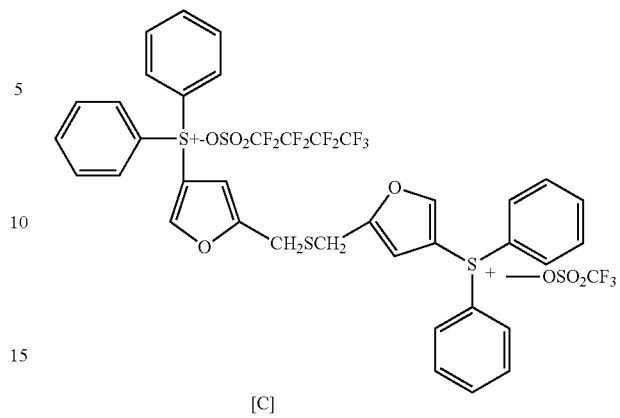

[C]

3) 10 g (10.6 mmol) of the diphenyl[(diphenylfurfurylsulfidyl)sulfonium triflate]dimer (compound A in the following reaction scheme 9) produced in Synthesis Example 4-2) was placed in a flask and was dissolved in dichloromethane. Subsequently, 5.1 g (15.9 mmol) of nonafluorobutane sulfonic acid sodium salt (compound B in the following reaction scheme 9) dissolved in distilled water was introduced into the above-prepared solution, and thus a reaction mixture liquid was prepared.

The reaction mixture liquid was stirred for 3 hours at normal temperature (25° C.), and the completion point of the reaction was checked by $^{19}$F-NMR. The reaction mixture liquid thus obtained was washed two or more times with distilled water and then was distilled under reduced pressure to remove the solvent. The reaction product was solidified using dichloromethane and hexane.

Diphenyl[(diphenylfurfuryl sulfide)sulfonium triflate]sulfonium nonaflate (compound C in the following reaction scheme 9) was obtained from the solidified reaction product, as a white solid in an amount of 9.2 g (yield: 79%).

[Reaction Scheme 9]

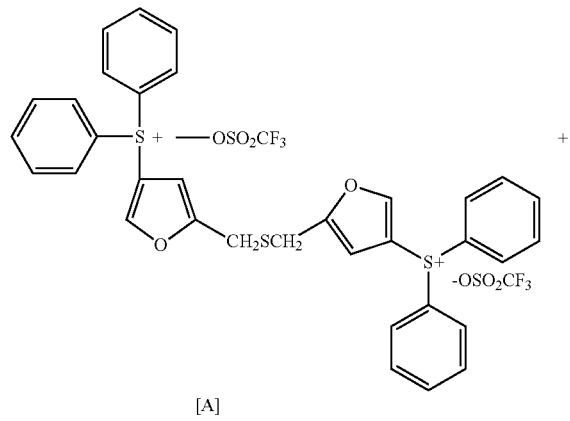

Synthesis Example 5

1) A reaction mixture liquid was prepared by dissolving 10 g (96 mmol) of tetrahydrothiophene 1-oxide, compound A in the following reaction scheme 10) and 16.32 g (96 mmol) of diphenyl ether (compound B in the following reaction scheme 10) in dichloromethane in a flask.

The flask containing the reaction mixture liquid was placed in a bath containing dry ice and acetone, and thus the temperature of the content of the flask was lowered.

When the temperature of the dry ice bath reached −40° C., 40 ml of triflic anhydride (compound C in the following reaction scheme 10) was slowly added dropwise to the flask to prepare a reaction solution.

After completion of the dropwise addition, while the temperature of the reactor was maintained at about −40° C., the reaction was carried out for 2 hours. The completion point of the reaction was checked by TLC, and when it was confirmed that the reaction was completed, the reaction solution was neutralized with an aqueous solution of $K_2CO_3$ to make the reaction solution alkaline.

The alkaline reaction solution was washed two times with distilled water, and then the solvent was evaporated under reduced pressure. The resulting crude reaction liquid concentrate was purified using dichloromethane and hexane. Thus, a purified reaction liquid concentrate was obtained.

Cyclopentyl(diphenyl ether)sulfonium triflate (compound D in the following reaction 10) was obtained from the purified reaction liquid concentrate, in an amount of 25 g (yield: 64%).

[Reaction Scheme 10]

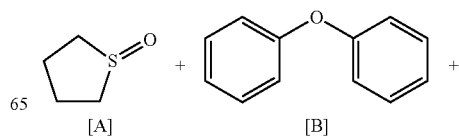

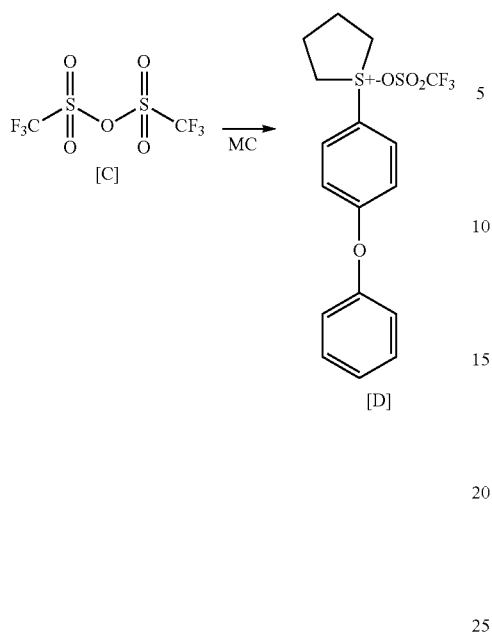

2) The reaction was carried out in the same manner as in Synthesis Example 5-1), except that 10 g (24.6 mmol) of cyclopentyl(diphenyl ether)sulfonium triflate (compound A in the following reaction scheme 11) produced in Synthesis Example 5-1) and 4.8 g (24.6 mmol) of phenyl sulfoxide (compound B in the reaction scheme 11) were dissolved in dichloromethane in a flask, and thus a reaction mixture liquid was prepared. Thus, diphenyl[cyclopentyl(diphenyloxidyl)sulfonium triflate]sulfonium triflate (compound C in the following reaction scheme 11) was obtained as a white solid in an amount of 13 g (yield: 71%).

[Reaction Scheme 11]

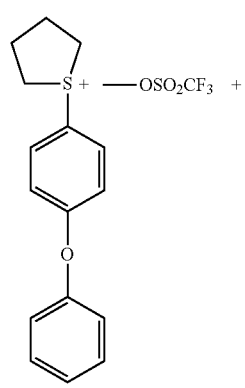

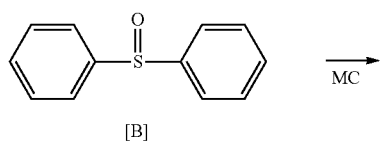

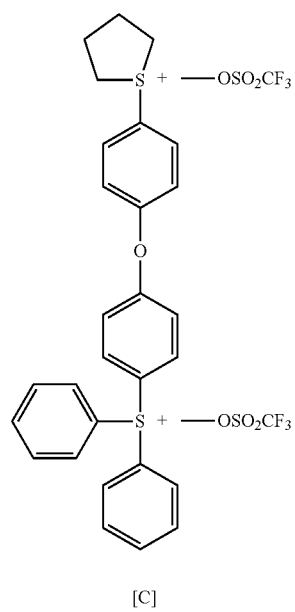

3) 10 g (13.5 mmol) of diphenyl[cyclopentyl(diphenyloxidyl)sulfonium triflate]sulfonium triflate (compound A in the following reaction scheme 12) produced in Synthesis Example 5-2) was placed in a flask and was dissolved in dichloromethane. Subsequently, 2.2 g (6.75 mmol) of nonafluorobutane sulfonic acid sodium salt (compound B in the following reaction scheme 12) was dissolved in distilled water, and thus a reaction solution was prepared.

The reaction solution was stirred for 3 hours at normal temperature (25° C.). The reaction completion point of the reaction solution was checked by $^{19}$F-NMR. The reaction solution thus obtained was washed two or more times with distilled water, and then was distilled under reduced pressure to remove the solvent. The reaction product was solidified using dichloromethane and hexane.

Diphenyl[cyclopentyl(diphenyloxidyl)sulfonium triflate]sulfonium nonaflate (compound C in the following reaction scheme 12) was obtained from the solidified reaction product, as a white solid in an amount of 9.2 g (yield: 76%).

$^{1}$H-NMR (CDCl3-d1): (ppm) 2.5 (m, 4H), 3.6 (t, 2H), 4.2 (t, 2H), 7.0-7.2 (dd, 4H), 7.3 (d, 2H), 7.4 (d, 2H), 7.6~7.8(m, 10H)

[Reaction Scheme 12]

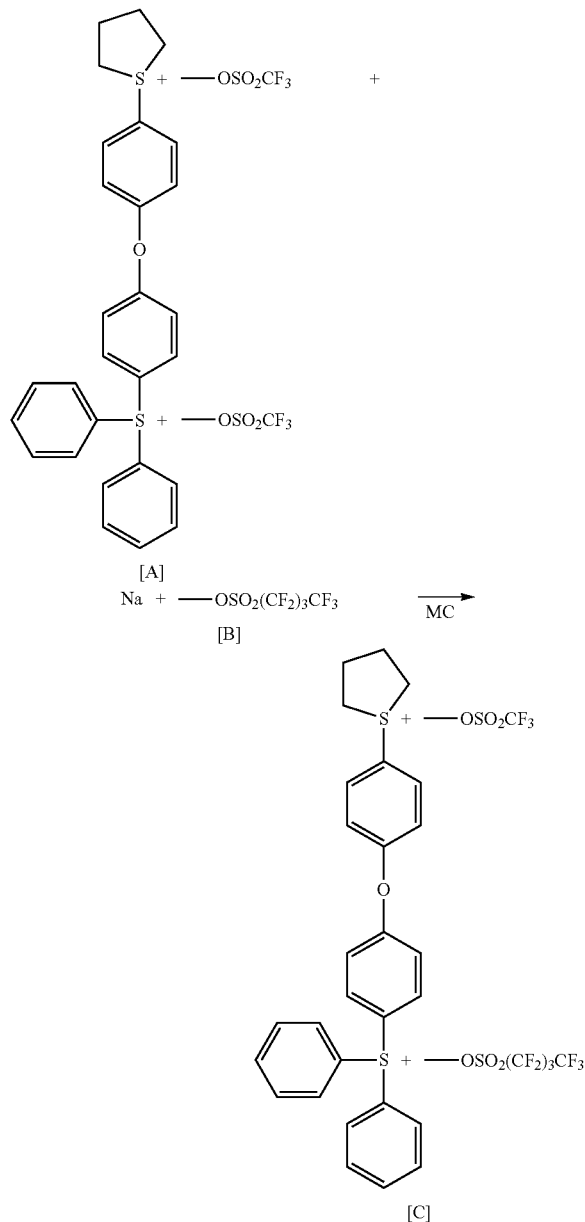

[Chemical Formula 6]

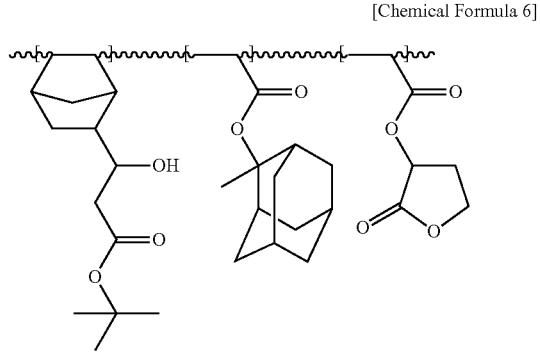

Synthesis Example for Resin 3-(Bicyclo[2.2.1]hept-5-en-2yl-3-hydroxypropionic acid t-butyl ester (BHP), 1-methyladamantane acrylate, and γ-butyrolactone methyl acrylate were filled in a reactor at a molar ratio of 1:1:1, and 1,4-dioxane was used as a polymerization solvent in an amount equivalent to 3 times the total mass of the reaction monomers. Azobisisobutyronitrile was used as an initiator at a proportion of 4 mol % relative to the total molar amount of the monomers. The mixture was allowed to react for 16 hours at 65° C.

The reaction solution after the reaction was precipitated in n-hexane and was dried in a vacuum, and thus a copolymer represented by the following formula (6) was obtained. The resin of the following formula (6) had a weight average molecular weight of 8,500.

Examples and Comparative Examples

Example 1

100 parts by weight of the resin obtained in the Synthesis Example for resin, 4 parts by weight of triphenylsulfonium triflate (triphenylsulfonium nonaflate) ether produced in Synthesis Example 1 (compound C in the above reaction scheme 2) as an acid generator, and 0.5 parts by weight of tetramethylammonium hydroxide as a basic additive were dissolved in 1,000 parts by weight of propylene glycol methyl ether acetate, and then the solution was filtered through a 0.2-μm membrane filter. Thus, a resist composition was prepared.

Example 2

A resist composition was prepared in the same manner as in Example 1, except that diphenyl[(diphenyl diphenyl ether) sulfonium triflate][adamantane-1-carboxylic acid-2,2-difluoro-2-sulfoethyl ester]sulfonium salt produced in Synthesis Example 2 (compound C in the above reaction scheme 3) was used as the acid generator.

Example 3

A resist composition was prepared in the same manner as in Example 1, except that diphenyl[(diphenyldiphenoxyethane) sulfonium triflate]sulfonium nonaflate produced in Synthesis Example 3 (compound C in the above reaction scheme 6) was used as the acid generator.

Comparative Example 1

A resist composition was prepared in the same manner as in Example 1, except that triphenylsulfonium triflate was used as the acid generator.

(Properties Evaluation of Examples and Comparative Example 1)

Each of the resist compositions of the Examples and Comparative Example was applied on a substrate using a spinner, and the resist composition was dried for 90 seconds at 110° C. to form a film having a thickness of 0.20 μm. The film thus formed was exposed using an ArF excimer laser stepper (lens aperture number: 0.78), and then was heat treated at 110° C. for 90 seconds.

The resist film that had been subjected to the exposure and heat treatment processes was developed for 40 seconds with a 2.38 wt % aqueous solution of tetramethylammonium hydroxide, and was washed and dried to form a resist pattern.

It was confirmed that the developability of the resist composition using an aqueous solution of tetramethylammonium hydroxide and the adhesiveness of the resist pattern to a substrate were satisfactory.

The results of the properties analysis of the Examples and Comparative Example are presented in the following Table 1.

In the case of the LER in the following Table 1, a 0.10-μm line-and-space (L/S) pattern was formed after development, and the roughness of the pattern was observed. The degree of improvement in terms of the LER was evaluated on the basis of a five-grade criteria from 1 to 5, relative to the pattern obtained in Comparative Example 1 which was rated as 1. A larger number means superior LER.

The sensitivity in the following Table 1 was measured by designating the amount of exposure which forms a 0.10-μm line-and-space (L/S) pattern at a line width of 1:1 after development, as the optimum amount of exposure, and the optimum amount of exposure was designated as the sensitivity. The minimum pattern dimension resolved at this time is indicated as the resolution.

(Properties evaluation of Example 1 and Comparative Example 2)

Each of the resist compositions was applied on a substrate using a spinner, and the resist composition was dried for 90 seconds at 110° C. to form a film having a thickness of 0.20 μm. The film thus formed was exposed using an ArF excimer laser stepper (lens aperture number: 0.78), and then was heat treated at 110° C. for 90 seconds.

The resist film that had been subjected to the exposure and heat treatment processes was developed for 40 seconds with a 2.38 wt % aqueous solution of tetramethylammonium hydroxide, and was washed and dried to form a resist pattern.

It was confirmed that the developability of the resist composition using an aqueous solution of tetramethylammonium hydroxide and the adhesiveness of the resist pattern to a substrate were satisfactory.

In the case of the LER in the following Table 2, a 0.10-μm line-and-space (L/S) pattern was formed after development, and the roughness of the pattern was observed. The degree of improvement in terms of the LER was evaluated on the basis

TABLE 1

| | Resin (100 parts by weight) | PAG type | Content of PAG (parts by weight) | Base (parts by weight) | Sensitivity (mJ/cm$^2$) | Resolution (nm) | LER |
|---|---|---|---|---|---|---|---|
| Example 1 | Copolymer of Synthesis Example for resin | Compound of Synthesis Example 1 | 4 | 0.5 | 14 | 60 | 4 |
| Example 2 | Copolymer of Synthesis Example for resin | Compound of Synthesis Example 2 | 4 | 0.5 | 13 | 80 | 3 |
| Example 3 | Copolymer of Synthesis Example for resin | Compound of Synthesis Example 3 | 4 | 0.5 | 12 | 70 | 3 |
| Comparative Example 1 | Copolymer of Synthesis Example for resin | Triphenylsulfonium triflate | 4 | 0.5 | 17 | 90 | 1 |

Comparative Example 2

100 parts by weight of the resin obtained in the Synthesis Example for resin, di[triphenylsulfonium triflate]ether produced in Synthesis Example 1-1 (formula (7) shown below) as an acid generator, and 0.5 parts by weight of tetramethylammonium hydroxide as a basic additive were dissolved in 1,000 parts by weight of propylene glycol methyl ether acetate, and then the solution was filtered through a 0.2-μm membrane filter to prepare a resist composition.

of a five-grade criteria from 1 to 5, relative to the pattern obtained in Comparative Example 2 which was rated as 1. A larger number means superior LER.

The sensitivity in the following Table 2 was measured by designating the amount of exposure which forms a 0.10-μm line-and-space (L/S) pattern at a line width of 1:1 after development, as the optimum amount of exposure, and the optimum amount of exposure was designated as the sensitivity. The minimum pattern dimension resolved at this time is designated as the resolution.

TABLE 2

| | Resin (100 parts by weight) | PAG type | Content of PAG (parts by weight) | Base (parts by weight) | Sensitivity (mJ/cm$^2$) | Resolution (nm) | LER |
|---|---|---|---|---|---|---|---|
| Example 1 | Copolymer of Synthesis Example for resin | Compound of formula (8) below | 4 | 0.5 | 14 | 60 | 4 |

TABLE 2-continued

| | Resin (100 parts by weight) | PAG type | Content of PAG (parts by weight) | Base (parts by weight) | Sensitivity (mJ/cm$^2$) | Resolution (nm) | LER |
|---|---|---|---|---|---|---|---|
| Comparative Example 2 | Copolymer of Synthesis Example for resin | Compound of formula (7) below | 4 | 0.5 | 12 | 90 | 1 |

Chemical Formula 7

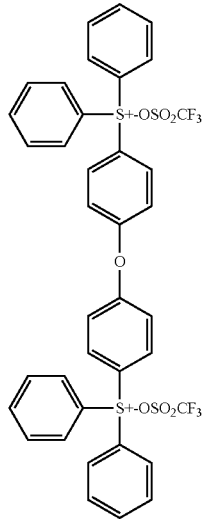

Chemical Formula 8

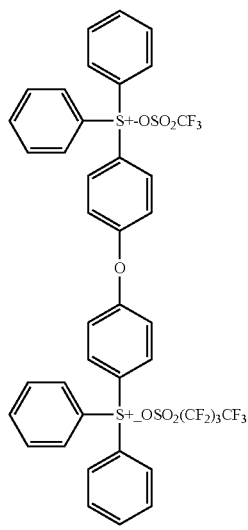

According to the results shown in Table 2, in the case of Comparative Example 2 in which the compound represented by the formula (7) was applied as a photo-acid generator, the sensitivity, resolution and LER were all poorer than in the case of Example 1. Thus, it could be confirmed that even though a sulfonium compound has two acid sites, if the sulfonium compound has identical anionic moieties, the sulfonium compound has inferior properties.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A photo-acid generator compound represented by the following formulas:

[Chemical Formula 4-1]

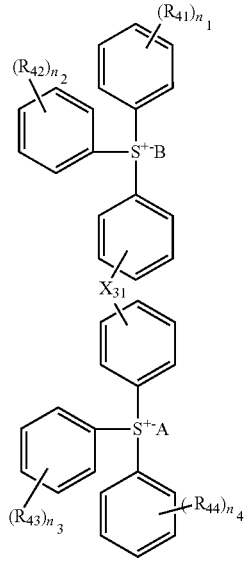

[Chemical Formula 4-2]

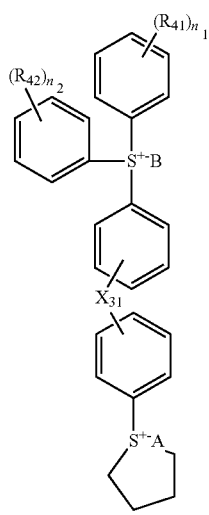

[Chemical Formula 4-3]

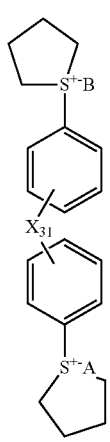

[Chemical Formula 4-4]

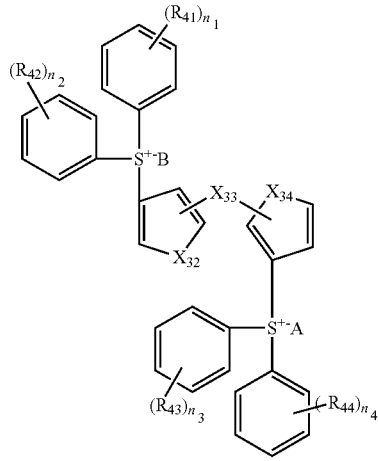

[Chemical Formula 4-5]

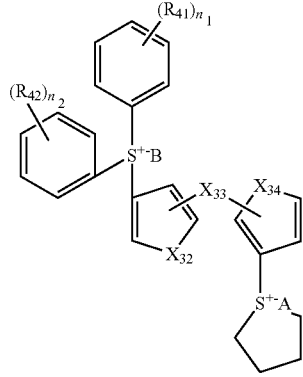

[Chemical Formula 4-6]

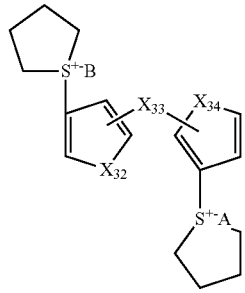

wherein in the photoacid generator compounds of formulas (4-1) to (4-6), $X_{31}$ represents any one selected from the group consisting of —O—, —OCH$_2$—, —OCH$_2$O—, —OCH$_2$CH$_2$O—, —O(C$_6$H$_4$)O—, —CH$_2$SCH$_2$— and —S(C$_6$H$_4$)S—;

$X_{32}$ and $X_{34}$ each independently represent any one selected from the group consisting of —O—;

$X_{33}$ represents any one selected from the group consisting of —O—, —OCH$_2$—, —OCH$_2$O—, —OCH$_2$CH$_2$O— and —CH$_2$SCH$_2$—;

$R_{41}$, $R_{42}$, $R_{43}$ and $R_{44}$ each independently represent any one selected from the group consisting of a hydrogen atom, an alkyl group having 1 to 5 carbon atoms, and a halogenated alkyl group having 1 to 5 carbon atoms;

$n_1$, $n_2$, $n_3$ and $n_4$ each independently represent an integer from 1 to 5; and $A^-$ and $B^-$ represent anions that are different from each other, and wherein the anions $A^-$ and $B^-$ each independently represent any one selected from the group consisting of $OSO_2CF_3^-$, $OSO_2C_4F_9^-$, $OSO_2C_8F_{17}^-$, $N(CF_3)_2^-$, $N(C_2F_5)_2^-$, $N(C_4F_9)_2^-$, $C(CF_3)_3^-$, $C(C_2F_5)_3^-$, $C(C_4F_9)_3^-$ and a compound represented by the following formula (1-4):

[Chemical Formula 1-4]

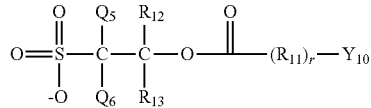

wherein in the formula (1-4),
- $Y_{10}$ represents any one selected from the group consisting of a cycloalkyl group, a heterocycloalkyl group, an aryl group, a heteroaryl group, an alkyl group, a heteroalkyl group, an allyl group, a perfluoroalkyl group, a haloalkyl group and an alkylsulfonyl group;
- $R_{11}$ represents any one selected from the group consisting of an alkanediyl group, an alkenediyl group, NR', S, O, CO and combinations thereof, while R' represents any one selected from the group consisting of a hydrogen atom and an alkyl group;
- $R_{12}$ and $R_{13}$ each independently represent any one selected from the group consisting of a hydrogen atom and an alkyl group having 1 to 8 carbon atoms;
- r represents an integer from 0 to 5; and
- $Q_5$ and $Q_6$ each independently represent a halogen atom.

2. The photo-acid generator according to claim 1, wherein the anion A– represents any one selected from the group consisting of $OSO_2CF_3^-$, $OSO_2CF_2CF_2CF_2CF_3^-$ and an anionic moiety represented by the following formula (1-5), and the anion B– represents any one selected from the group consisting of $OSO_2CF_3^-$, $OSO_2CF_2CF_2CF_2CF_3^-$ and an anionic moiety represented by the following formula (1-5):

[Chemical Formula 1-5]

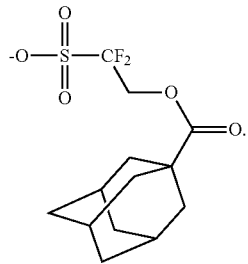

* * * * *